(12) United States Patent
Zwirn

(10) Patent No.: US 8,045,777 B2
(45) Date of Patent: Oct. 25, 2011

(54) CLUTTER SUPPRESSION IN ULTRASONIC IMAGING SYSTEMS

(75) Inventor: Gil Zwirn, Petach Tikva (IL)

(73) Assignee: Crystalview Medical Imaging Limited, St. Helier, Jersey, Channel Islands (GB)

( * ) Notice: Subject to any disclaimer, the term of this patent is extended or adjusted under 35 U.S.C. 154(b) by 1065 days.

(21) Appl. No.: 11/722,246

(22) PCT Filed: Dec. 27, 2005

(86) PCT No.: PCT/IL2005/001383
§ 371 (c)(1),
(2), (4) Date: Jun. 20, 2007

(87) PCT Pub. No.: WO2006/070362
PCT Pub. Date: Jul. 6, 2006

(65) Prior Publication Data
US 2008/0262352 A1    Oct. 23, 2008

Related U.S. Application Data

(60) Provisional application No. 60/640,368, filed on Dec. 30, 2004.

(51) Int. Cl.
*G06K 9/00* (2006.01)

(52) U.S. Cl. ........ 382/131; 382/128; 382/130; 600/437; 600/440; 600/443; 600/450; 600/454; 600/459

(58) Field of Classification Search ............... 600/440, 600/443, 450, 454, 459; 642/377; 382/128, 382/130, 131
See application file for complete search history.

(56) References Cited

U.S. PATENT DOCUMENTS

| 6,126,604 A | 10/2000 | Bae |
| 6,251,074 B1 | 6/2001 | Averkiou et al. |
| 6,705,993 B2 | 3/2004 | Ebbini et al. |
| 2003/0210179 A1 | 11/2003 | Dizaji et al. |

FOREIGN PATENT DOCUMENTS

| JP | 09164138 A | 6/1997 |
| WO | 2003079037 A2 | 9/2003 |
| WO | WO 2006/007362 A3 | 7/2006 |

OTHER PUBLICATIONS

International Search Report for PCT/IL05/01383.
International Preliminary Report on Patentability for PCT/IL05/01383.
Written Opinoin for for PCT/IL05/01383.
Krishna et al in a paper entitled "Subharmonic Generation from Ultrasonic Contrast Agents", Physics in Medicine and Biology, vol. 44, 1999, pp. 681-694.

(Continued)

*Primary Examiner* — Tse Chen
*Assistant Examiner* — Baisakhi Roy
(74) *Attorney, Agent, or Firm* — Martin Fleit; Paul D. Bianco; Fleit Gibbons Gutman Bongini & Bianco PL

(57) ABSTRACT

A method for ultrasonic imaging includes transmitting ultrasonic radiation toward a target and receiving the ultrasonic radiation reflected from a region of the target. A main reflected signal and an auxiliary reflected signal are defined. The reflected signals have different respective main and auxiliary beam patterns. A difference between the main reflected signal and the auxiliary reflected signal is taken, so as to generate an output signal containing a reduced level of clutter in comparison with the main reflected signal.

40 Claims, 19 Drawing Sheets

OTHER PUBLICATIONS

Spencer et al. in a paper entitled "Use of Harmonic Imaging without Echocardiographic Contrast to Improve Two-Dimensional Image Quality", American Journal of Cardiology, vol. 82, 1998, pp. 794-799.

Zwirn and Akselrod present in a paper entitled "Stationary Clutter Rejection in Echocardiography,", Presented at the European Study Group on Cardiovascular Oscillations (ESGCO), Leuven, Belgium, May 2004.

Herment et al. in a paper entitled "Improved Estimation of Low Velocities in Color Doppler Imaging by Adapting the Mean Frequency Estimator to the Clutter Rejection Filter", IEEE Transactions on Biomedical Engineering, vol. 43, 1996, pp. 919-927.

Book by Farina (1992), Chapter 4 (SLC system), pp. 95-103.

Gil Zwirn and Akselrod, Ultra sound un Med. and Biol., vol. 32, 2006 No. 1, pp. 43-52.

European Search Report for the corresponding European application No. 05819236.0 completed on May 18, 2010.

Office Action issued on Jun. 26, 2011 for corresponding Japanese application No. 2007-548960.

Letter dated Jun. 21, 2011 from Japanese associate to client providing a brief explanation of Examiners objections raised in Office Action issued Jun. 26, 2011 for corresponding Japanese application No. 2007-548960.

CLUTTER SUPPRESSION IN ULTRASONIC IMAGING SYSTEMS

This Application is the U.S. National Stage of International Application No. PCT/IL2005/001383, filed 27 Dec. 2005, which in turn claims benefit of priority from U.S. Provisional Patent Application No. 60/640,368, filed on Dec. 30, 2004.

CROSS-REFERENCE TO RELATED APPLICATIONS

This application is related to U.S. Provisional Patent Application 60/534,390, filed Jan. 7, 2004, whose disclosure is incorporated herein by reference.

FIELD OF THE INVENTION

The present invention relates generally to medical imaging systems, and particularly to methods and systems for suppressing clutter effects in ultrasonic imaging systems.

BACKGROUND OF THE INVENTION

Ultrasonic medical imaging plays a crucial role in modern medicine, gradually becoming more and more important as new developments enter the market. One of the most common imaging applications is echocardiography, or ultrasonic imaging of the cardiac system, providing essential anatomic and functional information on-line. Ultrasonic imaging systems typically produce noisy images, making the diagnosis of these images a task for highly trained expert physicians. One of the most problematic imaging artifacts is clutter, i.e., undesired information that appears in the imaging plane, obstructing the data of interest.

A common method for enhancing the visibility of the desired ultrasonic image relative to the clutter, particularly in patients with low echogenicity (a common phenomenon among obese patients), is administering contrast agents. Such agents enhance the ultrasonic backscatter from blood and aid in its differentiation from the surrounding tissue. This method is described, for example, by Krishna et al., in a paper entitled "Subharmonic Generation from Ultrasonic Contrast Agents," Physics in Medicine and Biology, vole 44, 1999, pages 681-694, which is incorporated herein by reference.

Using harmonic imaging instead of fundamental imaging, i.e., transmitting ultrasonic signals at one frequency and receiving at twice the transmitted frequency, also reduces clutter effects. Spencer et al. describe this method in a paper entitled "Use of Harmonic Imaging without Echocardiographic Contrast to Improve Two-Dimensional Image Quality," American Journal of Cardiology, vol. 82, 1998, pages 794-799, which is incorporated herein by reference.

Furthermore, image-processing methods have been developed for detecting clutter-affected pixels in echocardiographic images by means of post-processing. Zwirn and Akselrod present such a method in a paper entitled "Stationary Clutter Rejection in Echocardiography," presented at the European Study Group on Cardiovascular Oscillations (ESGCO), Leuven, Belgium, May 2004.

An additional class of currently available methods for handling clutter is a family of Clutter Rejection (CR) algorithms, used in Color-Doppler flow imaging. These methods estimate the flow velocity inside the cardiac chambers or other blood vessels and suppress the effect of slow-moving objects; assuming that the blood flow velocity is significantly higher than the motion velocity of the surrounding tissue. These methods are described, for example, by Herment et al. in a paper entitled "Improved Estimation of Low Velocities in Color Doppler Imaging by Adapting the Mean Frequency Estimator to the Clutter Rejection Filter," IEEE Transactions on Biomedical Engineering, vol. 43, 1996, pages 919-927.

In spite of the tremendous need and advantage for appropriate clutter suppression, there is no clutter suppression method that is devoid of the above limitations.

SUMMARY OF THE INVENTION

Embodiments of the present invention provide methods and devices for reducing clutter effects in ultrasonic imaging systems. The disclosed methods are particularly robust in differentiating the clutter from the desired signals, as the methods use signal processing during acquisition of the ultrasound image, as opposed to post-acquisition image-processing methods. In other words, the clutter is suppressed out by processing the received signal samples directly during data acquisition, rather than performing post-processing of the image pixels.

In some embodiments of the present invention, an ultrasound scanner transmits an ultrasound radiation beam into an area of interest in a patient's body using a probe comprising an array of transducers, such as piezo-electric elements. Reflected beams are received by the probe. In one embodiment, the probe comprises two receiving channels denoted main and auxiliary receiving channels. Each transmitting and receiving channel utilizes a predetermined beam pattern, typically implemented by using a different apodization of the transducers, as will be explained hereinbelow.

The output of the auxiliary receiving channel is subtracted coherently from the output of the main receiving channel to produce an output signal having reduced clutter content. Before performing the subtraction, the auxiliary receiving channel output is typically multiplied by a complex weight, i.e., a constant comprising amplitude and phase. The value of the complex weight is calculated so as to minimize the clutter level in the output signal.

The subtraction of the auxiliary receiving channel from the main receiving channel can also be viewed geometrically as forcing adaptive nulls into the beam pattern of the main receiving channel, in the directions and ranges of the undesired reflector or reflectors causing the clutter.

In some embodiments, the reflected signals received from the main and auxiliary receiving channels arm averaged over several frames. An algebraic equation is then solved, using the averaged reflected signals, in order to calculate an optimal complex weight that minimizes the clutter level in the output signal. In another embodiment, a minimum value of the reflected signals is used as an alternative to averaging the signals.

In some embodiments, the disclosed methods may be implemented using an existing ultrasound scanner, by changing the control of the probe and applying different processing to the signal samples during data acquisition.

The disclosed methods provide an additional benefit of reducing the dynamic range of the output signal produced by the transducer array, consequently eliminating clutter-affected regions in the image that typically have extremely bright gray-levels. Elimination of these bright regions leads to a more balanced image, in terms of gray-levels, and enhanced overall image quality.

There is therefore provided, in accordance with an embodiment of the present invention, a method for ultrasonic imaging, including:

transmitting ultrasonic radiation toward a target and receiving the ultrasonic radiation reflected from a region of the target so as to define a main reflected signal and an auxiliary reflected signal having different, respective main and auxiliary beam patterns; and taking a difference between the main reflected signal and the auxiliary reflected signal so as to generate an output signal containing a reduced level of clutter in comparison with the main reflected signal.

In a disclosed embodiment, receiving the ultrasonic radiation includes receiving the reflected ultrasonic radiation using an array of transducers, and multiplying outputs of the transducers by respective first and second pluralities of apodization coefficients, in accordance with the main and auxiliary beam patterns, in order to define the main and auxiliary reflected signals.

In another embodiment, receiving the ultrasonic radiation includes defining a plurality of auxiliary reflected signals.

Additionally or alternatively, the main beam pattern is narrower than the auxiliary beam pattern.

In another disclosed embodiment, taking the difference includes:

calculating a complex weight responsively to the reflected signals;

multiplying the auxiliary received signal by the complex weight to obtain a result; and subtracting the result from the main reflected signal so as to produce the output signal.

Additionally or alternatively, calculating the complex weight includes averaging the reflected signals over multiple image frames and determining the complex weight based on the averaged reflected signals.

Further additionally or alternatively, calculating the complex weight includes taking a minimum value of the reflected signals over multiple image frames, and determining the complex weight based on the minimum value.

In another disclosed embodiment, multiplying the auxiliary received signal by the complex weight and subtracting the result include determining a combined beam pattern responsively to the complex weight and to the main and auxiliary beam patterns and applying the combined beam pattern to the main reflected signal.

In yet another disclosed embodiment, receiving the ultrasonic radiation includes collecting the reflected ultrasonic radiation in each image frame at multiple different settings of range and angle, and calculating the complex weight includes calculating a respective complex weight value for each of the different settings of the range and angle.

In still another disclosed embodiment, taking the difference includes calculating a phase difference between the main reflected signal and the auxiliary reflected signal, and forcing a null at an angle responsive to the phase difference in an effective beam pattern corresponding to the output signal.

Additionally or alternatively, forcing the null includes forcing the null only if the angle is within a predetermined range.

In an aspect of the present invention, an improved image is generated responsively to the output signal and displaying the improved image to a user.

In another aspect of the invention, the output signal has a reduced dynamic range relative to the main reflected signal.

In some embodiment of the invention, there is provided a method for reducing clutter, including normalizing a magnitude of the main reflected signal to a magnitude of the output signal and taking a minimum value per cell between the magnitude of the main reflected signal and the magnitude of the output signal.

In another disclosed embodiment, a magnitude of each of the main reflected and output signals is organized into two dimensional arrays; a y axis of a cell range and an x axis of a cell angle is established; at least one two-dimensional block is determined by at least three cells along the y axis and by at least three cells along the x axis; a center cell within each at the least one two dimensional block is defined; a mean magnitude of the at least one block is determined and a ratio between the mean magnitude of the at least one block and the magnitude of the center cell for each of the magnitude of the main reflected signal array and the magnitude of the output signal array is calculated.

In some exemplary embodiment of the invention, the ratio of the magnitude ratio of the output signal array is divided by the ratio of the magnitude of the main reflected signal array; and the divided ratio is compared with a threshold of the ratio of the output signal and the main reflected signal ratio.

In an exemplary embodiment, this includes replacing the output signal magnitude by the main reflected signal magnitude for the center cell if the divided ratio exceeds the threshold.

In an additional embodiment, a magnitude of each of the main reflected and output signals is organized into two dimensional arrays; a y axis of a cell range and an x axis of a cell cross range is established; at least one two-dimensional block is determined by at least three cells along the y axis and by at least three cells along the x axis; a center cell within each at the least one two dimensional block is defined; a mean magnitude of the at least one block is determined and a ratio between the mean magnitude of the at least one block and the magnitude of the center cell for each of the magnitude of the main reflected signal array and the magnitude of the output signal array is calculated.

In some exemplary embodiment of the invention, the ratio of the magnitude ratio of the output signal array is divided by the ratio of the magnitude of the main reflected signal array; and the divided ratio is compared with a threshold of the ratio of the output signal and the main reflected signal ratio.

Further, in an exemplary embodiment, this includes replacing the output signal magnitude by the main reflected signal magnitude for the center cell if the divided ratio exceeds the threshold.

In another embodiment, a magnitude of each of the main reflected and output signals is organized into three dimensional arrays; a y axis of a cell range, an x axis of a cell angle in azimuth and a z axis of a cell angle in elevation are established; at least one three-dimensional block is determined by at least three cells along the x, y and z-axes; a center cell within each at the least one three dimensional block is defined; a mean magnitude of the at least one block is determined and a ratio between the mean magnitude of the at least one block and the magnitude of the center cell for each of the magnitude of the main reflected signal array and the magnitude of the output signal array is calculated.

In some exemplary embodiment of the invention, the ratio of the magnitude ratio of the output signal array is divided by the ratio of the magnitude of the main reflected signal array; and the divided ratio is compared with a threshold of the ratio of the output signal and the main reflected signal ratio.

Further, in an exemplary embodiment, this includes replacing the output signal magnitude by the main reflected signal magnitude for the center cell if the divided ratio exceeds the threshold.

In an additional embodiment, a magnitude of each of the main reflected and output signals is organized into three dimensional arrays; a y axis of a cell range, an x axis of a cell cross range in azimuth and a z axis of a cell cross range in elevation are established; at least one three-dimensional block is determined by at least three cells along the x, y and z-axes; a center cell within each at the least one three dimensional block is defined; a mean magnitude of the at least one block is determined and a ratio between the mean magnitude of the at least one block and the magnitude of the center cell for each of the magnitude of the main reflected signal array and the magnitude of the output signal array is calculated.

In some exemplary embodiment of the invention, the ratio of the magnitude ratio of the output signal array is divided by the ratio of the magnitude of the main reflected signal array; and the divided ratio is compared with a threshold of the ratio of the output signal and the main reflected signal ratio.

Further, in an exemplary embodiment, this includes replacing the output signal magnitude by the main reflected signal magnitude for the center cell if the divided ratio exceeds the threshold.

There is additionally provided, in accordance with an embodiment of the present invention, apparatus for ultrasonic imaging, including:

a probe, which is adapted to transmit ultrasonic radiation toward a target and to receive the ultrasonic radiation reflected from a region of the target so as to define a main reflected signal and an auxiliary reflected signal having different, respective main and auxiliary beam patterns; and a scanner, which is adapted to take a difference between the main reflected signal and the auxiliary reflected signal so as to generate an output signal containing a reduced level of clutter in comparison with the main reflected signal.

There is also provided, in accordance with an embodiment of the present invention, a computer software product for use in conjunction with a probe, which transmits ultrasonic radiation toward a target and generates signals in response to the ultrasonic radiation reflected from a region of the target, the product including a computer-readable medium in which program instructions are stored, which instructions, when read by a computer, cause the computer to process the signals so as to define a main reflected signal and an auxiliary reflected signal having different, respective main and auxiliary beam patterns, and to take a difference between the main reflected signal and the auxiliary reflected signal so as to generate an output signal containing a reduced level of clutter in comparison with the main reflected signal.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The present invention will be more fully understood from the following detailed description of the embodiments thereof, taken together with the drawings in which:

BRIEF DESCRIPTION OF THE DRAWINGS

The invention for clutter suppression in ultrasonic imaging systems is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

System Description

Figure 1A:
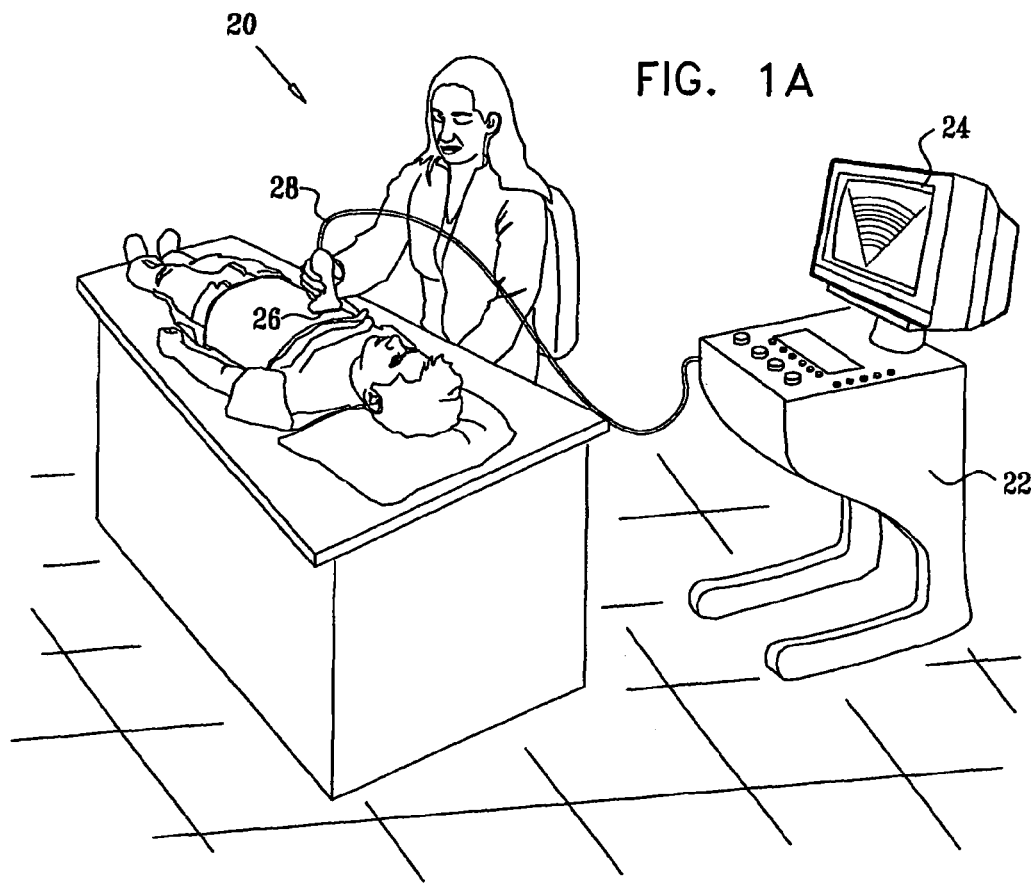
FIG. 1A is a schematic, pictorial illustration of an ultrasonic imaging system, in accordance with an embodiment of the present invention.

In broad terms, the present invention relates to methods and systems for suppressing clutter effects in ultrasonic imaging systems.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1A is a schematic, pictorial illustration of an ultrasonic imaging system 20, in accordance with an embodiment of the present invention.

System 20 comprises an ultrasound scanner 22 that scans internal organs of a patient using ultrasound radiation. A display unit 24 displays the scanned images. A probe 26, connected to scanner 22 by a cable 28, is typically held against the patient body in order to image a particular body structure, such as the heart (referred to as a "target"). Alternatively, the probe may be adapted for insertion into the body, such as a transesophageal probe. The probe transmits and receives the ultrasound beams required for imaging. Scanner 22 comprises control and processing circuits for controlling probe 26 and processing the signals received by the probe.

Figure 1B:
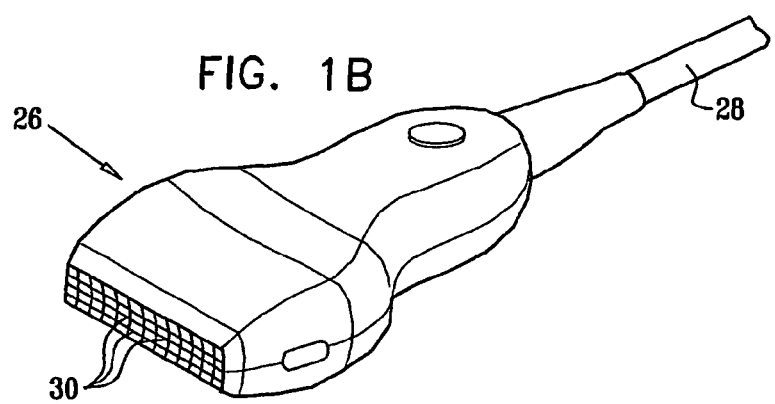
FIG. 1B is a schematic, pictorial illustration of a probe used in an ultrasonic imaging system, in accordance with an embodiment of the present invention.

FIG. 1B is a schematic, pictorial illustration of probe 26 used in imaging system 20, in accordance with an embodiment of the present invention. The probe comprises an array of piezoelectric transducers 30, which are configured to operate as a phased array. On transmission, each transducer converts an electrical signal produced by scanner 22 into a beam of ultrasound radiation transmitted into the patient's body. On reception, the transducers receive the ultrasound radiation reflected from different body tissues, and convert it into electrical signals sent to scanner 22 for processing.

Probe 26 typically comprises several dozens and up to several hundreds of transducers 30 arranged in a horizontal linear array. The horizontal aperture of the array, typically in the order of 2 centimeters, provides the horizontal beamwidth of the probe and the resulting horizontal angular resolution. Some probes, referred to as "1½ dimensional probes," also comprise several rows of transducers in the vertical dimension, providing a vertical sector-like beam pattern. Other probes comprise a complete two-dimensional array of transducers, enabling both horizontal and vertical directional beam patterns. Such probes enable the scanner to perform three-dimensional scanning. The terms "horizontal" and "vertical" are used here solely for convenience, as the array may be positioned during imaging in any appropriate orientation relative to the patient's body.

The array of transducers is used to form several transmission and reception beam patterns, and respective transmitting and receiving channels. Several beam patterns may be synthesized using a single array of transducers, by applying different apodizations. On reception, apodization is a process of multiplying the output signal of each transducer by a multiplicative complex coefficient ("apodization coefficient"), before combining the outputs of all transducers to generate an overall array output signal. A reciprocal process is performed on transmission. (In many cases a constant apodization is used on transmission).

In a disclosed embodiment, the apodization to be applied to the auxiliary receiving channel is determined based on the common clutter directions. The inventor has found that the majority of the clutter originates from objects that are relatively far from the region of interest. This behavior is due to the basic anatomy of the human torso and to the typical positioning of the probe in an echocardiographic measurement. (The probe is typically placed between the ribs or beside them. If the probe were placed directly on top of the ribs, there would be no relevant returned signal from the cardiac muscle.)

Consequently, the apodization of the auxiliary receiving channel is set so as to produce a beam pattern having a wide main-lobe. Since the effective width (aperture) of the array of transducers is inversely proportional to the angular width of its main-lobe, this requirement is equivalent to using a narrow apodization window. The following method may be used (refer also to typical beam patterns shown in FIG. 3 below):

The gain of the auxiliary channel beam pattern is set to be lower than the gain of the main channel beam pattern for all angles corresponding to the main-lobe of the main channel beam pattern.

The gain of the auxiliary channel beam pattern is set to be higher than the gain of the main channel beam pattern for all angles corresponding to the dominant side-lobes of the main channel beam pattern.

The relevant beam patterns to consider are the two-way transmit-receive patterns. In order to achieve the desired wide auxiliary receiving channel beam pattern, it is desirable to transmit using a wide beam pattern as well. This constraint is not problematic, however, since the need for high refresh rates, especially in three-dimensional ultrasonic imaging, has led to the common use of multiple receive beams for each transmit beam, which also requires wide transmit beam patterns, albeit for purposes other than those of the present invention.

Many three-dimensional ultrasound systems transmit using a single, wide beam pattern and receive simultaneously using a large number (typically 32 or 64) of sectorized receiving beam patterns, each beam pattern covering a separate angular sector. When applying the disclosed clutter suppression methods to an ultrasound system having N receiving beam patterns, N respective auxiliary receiving channels are typically used. Additional transmitting channels may also be used, ranging from one additional common transmitting beam pattern up to N additional beam patterns for optimum performance.

In alternative probe designs the transducers are arranged in a convex, rather than linear, array. Although the embodiments disclosed herein describe a linear array probe for the sake of conceptual clarity, the disclosed methods may be used in conjunction with any suitable probe design.

In some embodiments, the disclosed method may be implemented as a software retrofit or enhancement to the software of an existing ultrasound scanner, utilizing the existing probe. The existing scanner typically comprises a computer, which is programmed in software to carry out the functions described herein. (Scanner 22 may similarly comprise a computer of this sort.) The software may be downloaded to the computer in electronic form, over a network, for example, or it may alternatively be supplied to the computer on tangible media, such as CD-ROM. Further alternatively, the method described herein may be implemented in dedicated hardware logic, or using a combination of hardware and software elements.

Although the embodiments described herein use two receiving channels, other embodiments comprising additional auxiliary receiving channels or additional transmitting channels may be used, enabling additional degrees of freedom, and enabling simultaneous suppression of multiple clutter reflectors and/or clutter reflectors having significant angular widths. The generalized case of multiple auxiliary receiving channels is described in Appendix 2 hereinbelow.

Figure 2:
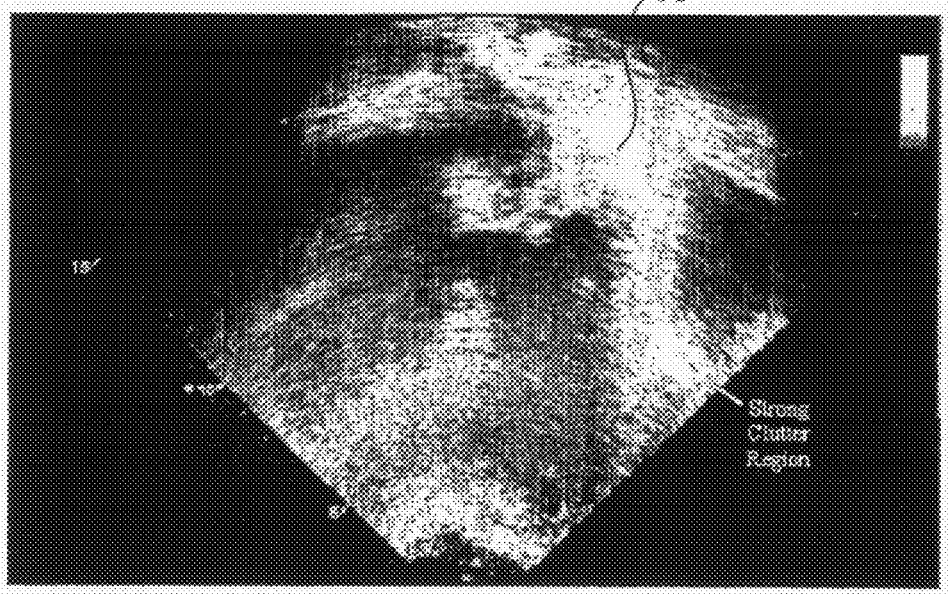
FIG. 2 is an ultrasonic image demonstrating clutter effects.

FIG. 2 is an image 32 demonstrating strong clutter effects in an ultrasonic image without clutter suppression. Image 32 is a typical echocardiographic image, scanning the patient's cardiac region. The intensity of the reflected signals is represented by gray-levels in the image, with stronger reflections shown as brighter gray-levels. A strong clutter region 34 can be seen as a white region.

There are two major origins for clutter in echocardiography and in ultrasonic imaging in general. The first is effective imaging of off-axis objects, located outside the desired region of interest. Most of the off-axis energy is received from highly reflective objects through the probe transducer side-lobes, as will be explained hereinbelow. For example, in echocardiography the dominant reflectors are typically the ribcage and the lungs. The second origin of clutter is multi-path reflections, also called reverberations. In some cases, the geometry of the scanned tissue with respect to the probe, as well as the local reflective characteristics of the tissue, causes a noticeable percentage of the transmitted energy to bounce back and forth in the tissue before reaching the probe. As a result, the signal measured at a specific range-gate includes contributions from incorrect ranges, in addition to the desired range. If the signal from the incorrect regions corresponds to an object having high reflectivity, it may have a significant effect on the image quality.

The clutter in the example shown in FIG. 2 is the result of strong reflections from the ribcage. The methods described below may be used to reduce this clutter effect in order to provide a clearer image of the heart.

Figure 3:
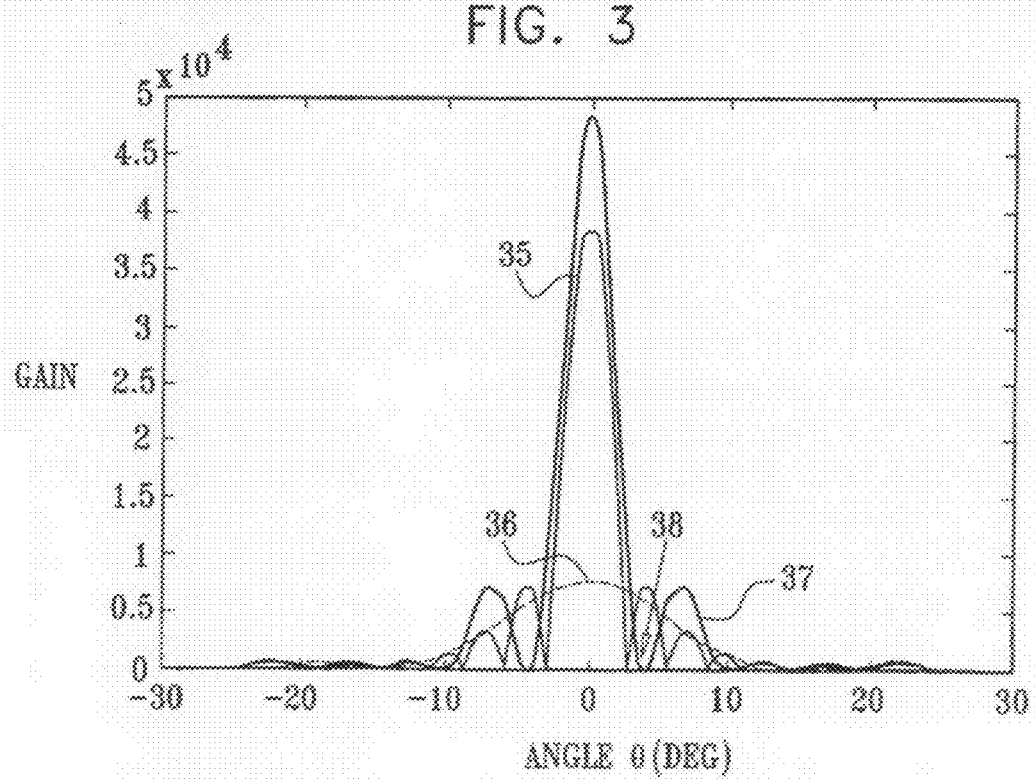
FIG. 3 is a plot that schematically shows transducer array beam patterns, in accordance with an embodiment of the present invention.

FIG. 3 is a plot that schematically shows typical beam patterns used by the array of transducers 30 of probe 26, in accordance with an embodiment of the present invention. A curve 35 shows a narrow beam pattern, typically used as a main receiving channel beam pattern. Another curve 36 shows a wide beam pattern, typically used as a transmitting beam pattern and as an auxiliary receiving channel beam pattern. A curve 37 shows a geometrical representation of an effective beam pattern of the output signal, produced by taking a difference between the main and auxiliary beam patterns according to the method disclosed below. A forced null 38 can be seen in an angle corresponding to a dominant side-lobe of the narrow beam pattern shown in curve 35.

Clutter Suppression Method

Figure 4:
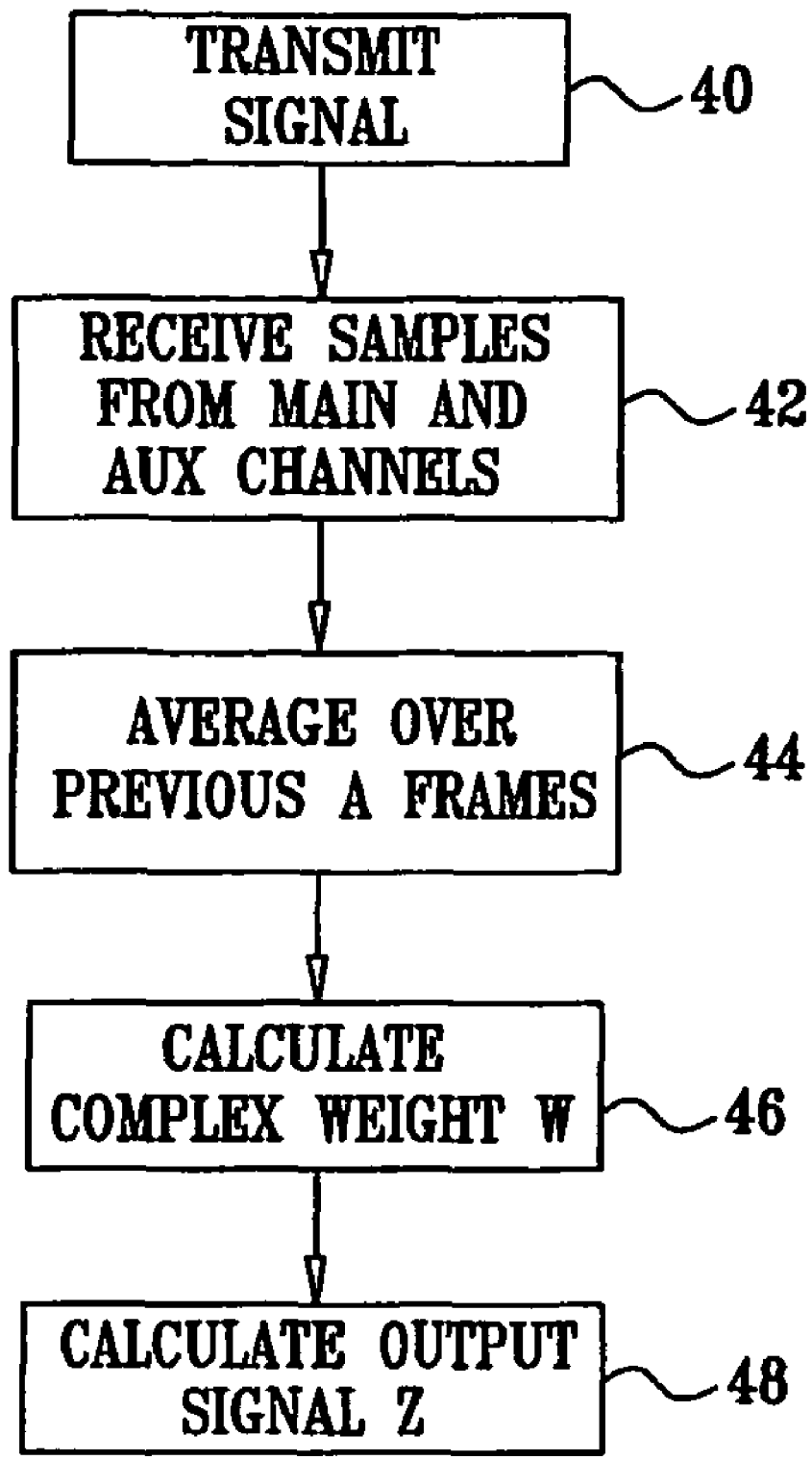
FIG. 4 is a flow chart that schematically illustrates a method for suppressing clutter effects, in accordance with an embodiment of the present invention.

FIG. 4 is a flow chart that schematically illustrates a method for suppressing clutter effects, in accordance with an embodiment of the present invention.

While the present description, for the sake of conceptual clarity, refers to a system comprising a single auxiliary receiving channel, the method described herein below may also be used in systems comprising multiple receiving channels.

Additional theoretical details, as well as a generalization of the disclosed method to the case of multiple receiving channels, can be found in Appendix 2 hereinbelow.

The method begins with scanner 22 transmitting a beam of ultrasound radiation into the patient's body using transducers 30 of probe 26, at a transmission step 40. Typically, the scanner sweeps the beam of radiation in a continuous manner over a chosen area or volume of the target, defined in terms of range-gates and angles. A single scan of the chosen area is referred to as a "frame" or a "refresh frame." The scanner scans successive frames continuously, to produce real time video-like images. The clutter suppression method described below is typically repeated for each angle and range-gate of the scan.

Reflected beams are received by the main and auxiliary receiving channels of the probe at a reception step 42. As explained above, the main and auxiliary reflected signals are received simultaneously by probe 26, and are generated by scanner 22 by multiplying the output signals from transducers 30 by main and auxiliary apodization coefficients, corresponding to the respective beam patterns chosen for each channel.

Each sample of the signal $V_M$ received by the main receiving channel, relating to a specific angle and range, comprises two components. The first component, denoted S, is the desired signal reflected from the region of interest. The second component, denoted $C_M$, originates from clutter, i.e., relates to irrelevant directions or ranges:

$$V_M = S + C_M$$

The following assumptions are made regarding the reflected signal characteristics:

1. Ultrasonic clutter typically originates from highly reflective elements that are not necessarily point-like (e.g., sections of the ribcage). Consequently, the clutter contribution is the integral over all irrelevant angles (and ranges), with each angle given a phase and magnitude according to the receiving channel beam pattern. Nevertheless, in most practical cases the clutter may still be represented as a single dominant reflector.
2. The clutter is typically strong in comparison with the level of the desired signal.
3. The temporal variation of clutter reflectors is typically slow compared to the frame refresh rate of the imaging system. In other words, the clutter autocorrelation time is relatively long. Hence, when considering a small number of consecutive frames, the clutter may be considered constant rather than random.
4. When moving structures, such as the heart, are imaged, the desired signal reflected from the region of interest has a relatively short autocorrelation time, due, for example, to the rapid cardiac wall motion. This effect is magnified by "speckle noise," characteristic of ultrasonic imaging, which causes significant signal variations even for slight movements.

The paper by Zwirn and Akselrod cited above reinforces these points by showing that clutter-affected pixels are characterized by high gray-level intensities (since strong clutter is more visible than weak clutter) and low temporal variability (i.e., the clutter gray-levels change only slightly during a single cardiac cycle).

As a result of the low temporal variability of the clutter, averaging the reflected signal corresponding to a certain clutter-affected range/angle setting over several imaging frames (typically on the order of 2 to 7 frames) considerably decreases the contribution of the desired signal, while maintaining the clutter contribution. For range/angle settings that are not affected by clutter, averaging the signal over several frames typically results in a very small output value, as long as the tissue in the region of interest shows some motion. Therefore, the disclosed method is particularly effective in imaging scenarios in which the scanned organs show a certain amount of motion, such as in echocardiography.

Returning to the description of FIG. 4, scanner 22 averages the main and auxiliary reflected signals corresponding to each range/angle setting over a predetermined number of frames at an averaging step 44. The main reflected signal, denoted $V_M$, is averaged over A consecutive frames to provide $\overline{V}_M$. Similarly, the auxiliary reflected signal, denoted $V_A$, is averaged over A consecutive frames to provide $\overline{V}_A$.

(In an alternative embodiment, particularly suitable for cases in which the scanned organs do not show a sufficient amount of motion, $\overline{V}_m$ and $\overline{V}_A$ are produced by taking the minimum values of $V_M$ and $V_A$, respectively, over A frames.)

Having averaged the two reflected signals, scanner 22 calculates the complex weight W for each given range/angle setting at a weight calculation step 46. W is given by:

$$W = \frac{\overline{V}_K}{\overline{V}_A}$$

Finally, the scanner calculates an output signal, denoted Z, for each range/angle setting at a subtraction step 48. Z is generated by multiplying the complex weight W by the auxiliary reflected signal $V_A$ and subtracting the result from the main reflected signal $V_M$:

$$Z = V_M - W V_A$$

Scanner 22 subsequently translates output signal Z to an image that is displayed by display unit 24 to the user. The translation typically uses a Brightness Transfer Function (BTF) that translates signal magnitudes into gray-level intensities.

The BTF is typically a logarithmic function, although any other suitable BTF may also be used.

In order for the method to function properly, sufficient dynamic range should be provided by the receiving channels. The received signals should not be saturated even for strong clutter reflections. A Time Gain Control (TGC) mechanism, whereby different gains are applied to the receiving channels at different points in the scan, may be used in system 20 for preventing saturation.

In another embodiment of the present invention, scanner 22 measures the angle-of-arrival, with respect to the probe bore-sight, from which the dominant reflected signals originate. Having identified the angle-of-arrival of a clutter reflection, the scanner may place a null pointing to a specific angular direction in the effective beam pattern corresponding to the output signal, thereby reducing the clutter level from this direction. The inventor has found that the phase difference between the main and auxiliary receiving beam patterns (and consequently the phase difference between signals received through these beam patterns) has a typical cosine form, as a function of the angle between the dominant reflector and the probe bore-sight. Hence, signals received through the main-lobe of the main receiving channel can be differentiated from other signals based on the aforementioned phase difference. For example, if $\alpha$ is the phase of the main-to-auxiliary ratio (i.e. the phase difference between the main and auxiliary receiving channels) at the null of the main receiving channel main-lobe, then signals received through the main-lobe typically have phases in the range $[0,\alpha]$.

In another embodiment, the angle-of-arrival measurement described above is used to selectively enable the clutter suppression method. In this embodiment the scanner performs clutter suppression only if the angle-of-arrival measurement determines that the dominant clutter originates from angles outside of the main receiving channel main-lobe. This limitation helps to avoid situations in which the clutter suppression method attempts to force a null into the main receiving channel main-lobe, and by doing so may deform the desired imaging signal. Note that even in the case of widely distributed clutter, against which a single null is ineffective, the clutter suppression methods described herein will give substantial signal enhancement as long as the clutter is stationary.

The translation of the complex measurements made by scanner 22 to the image displayed by the display unit 24 usually requires interpolation, to translate the range/angle data to Cartesian coordinates. Theoretically, the clutter suppression algorithm can be applied either directly to the sampled data, which is gathered as a function of range/angle, or to the Cartesian images used for display. In either case, the data from both channels must be complex. However, the clutter suppression outputs might show extreme phase changes between consecutive range or angle configurations. Therefore, the clutter suppression should preferably be applied directly to the samples, and the magnitude of the output should be used for interpolation.

Clutter suppression reduces the local signal magnitude so that discarding cells showing increased magnitude improves output. In additional exemplary embodiments, an average magnitude of the main reflected signal is normalized to an average magnitude of the output signal, and a minimum value per cell between the magnitude of the main reflected signal and the magnitude of the output signal is taken. For example, about 10 elements of the extreme highest magnitude will be discarded during averaging. In other cases, about 10 elements of the extreme lowest magnitude will be discarded during averaging.

Additionally, following clutter suppression, modifying (discarding) cells showing a lower magnitude than surrounding cells in both range and angle when compared to the original frame, improves output. This particularly occurs in cells showing low temporal variability. In exemplary embodiments, the discarding procedure includes organizing a magnitude of each of the reflected and output signals into two dimensional arrays.

For each of the magnitude of the main reflected signal array and the magnitude of the output signal array a y axis of a cell range and an x axis of a cell angle are established.

Alternatively, for each of the magnitude of the main reflected signal array and the magnitude of the output signal array a y axis of a cell range and an x axis of a cell cross range is established.

On both of the above two coordinate systems, a first including cell angle and a second including cell cross range, the following procedures are preformed:

1. Determining at least one two dimensional block defined by at least three cells along the y axis and by at least three cells along the x axis;
2. Determining a center cell within each at the least one two dimensional block; and
3. Determining a mean magnitude of the at least one block and calculating a ratio between the mean magnitude of the at least one block and the magnitude of the center cell.

In further exemplary embodiments, the magnitude ratio of the output signal array is divided by the magnitude ratio of the main reflected signal array, and the divided ratio is compared with a threshold of the ratio of the output signal ratio and the main reflected signal ratio.

In still further exemplary embodiments, the center cell of the output signal magnitude is replaced by the center cell of the main reflected signal magnitude if the divided ratio exceeds the threshold. In an exemplary embodiment using the cell range and cell angle, a threshold comprises about 10. For the case of using the cell range and cell cross range, possible threshold values are in the range 2.0 to 10.0, preferably 3.8 or 4.0.

In other exemplary embodiments, to be used for three-dimensional echocardiographic imaging, a procedure for cell modification includes organizing a magnitude of each of the reflected and output signals into three dimensional arrays.

For each of the magnitude of the main reflected signal array and the magnitude of the output signal array a y axis of a cell range, an x axis of a cell angle in azimuth and a z axis of a cell angle in elevation are established.

Alternatively, for each of the magnitude of the main reflected signal array and the magnitude of the output signal array a y axis of a cell range, an x axis of a cell cross range in azimuth and a z axis of a cell cross range in elevation are established.

On both of the above two coordinate systems, a first including cell angle in azimuth and a cell angle in elevation and a second including cell cross range in azimuth and a cell cross range in elevation, the following procedures are preformed:

1. Determining at least one three dimensional block defined by at least three cells along each of the x, y and z-axes;
2. Defining a center cell within each at least one three dimensional block; and
3. Determining a ratio between the mean magnitude of the at least one three dimensional block and the magnitude of the center cell for the magnitude of the main reflected signal array and the magnitude of the output signal array.

In further exemplary embodiments, the magnitude ratio of the output signal array is divided by the magnitude ratio of the main reflected signal array, and the divided ratio is compared with a threshold of the ratio of the output signal ratio and the main reflected signal ratio.

In still further exemplary embodiments, the center cell of the output signal magnitude is replaced by the center cell of the main reflected signal magnitude if the divided ratio exceeds the threshold. In an exemplary embodiment, using the cell range, cell angle in azimuth and cell angle in elevation, a threshold comprises about 10. For the case of using the call range, cross range in azimuth and cross range in elevation, possible threshold values are in the range 2.0 to 10.0, preferably 3.8 or 4.0.

In three-dimensional echocardiographic imaging systems, and in ultrasonic imaging systems in general, the processing of the receiving channels is typically optimized to provide sufficiently high frame refresh rates. In order to minimize additional strain on resources while increasing the utilization of receiving channels, the complex weight W may be updated only once every A frames, A>1.

In another embodiment, particularly suitable for cases in which averaging over A' frames (A'<A) produces acceptable results, a combined beam pattern corresponding directly to the output signal Z ($V_M$–$WV_A$) may be synthesized using a single receiving channel with an appropriate combined apodization. The combined apodization is given by $P_M$–$WP_A$, wherein $P_M$ and $P_A$ are the original apodizations producing the main and auxiliary receiving channels, respectively. The combined apodization is calculated and stored for each range/angle setting. When using this method, the complex weight W is recalculated only once every A' frames.

As used herein the term "about" refers to ±50%.

Although the embodiments described hereinabove relate specifically to echocardiographic imaging, the principles of the present invention may similarly be applied in ultrasonic imaging of other body organs, as well as in other, non-medical ultrasound applications.

Furthermore, it is expected that during the life of this patent many relevant delivery systems will be developed and the scope of the term Clutter Suppression is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

APPENDIX 1

System Simulation

The method described above was simulated by the inventor in order to prove its feasibility and performance. Exemplary simulation results are presented hereinbelow. The simulations are based on the FIELD-II Simulator for Ultrasound Systems, which is a standard tool for assessing commercial ultrasound technologies. The simulations assume the following configuration:

A two-dimensional transducer, which is composed of 64×26 elements.

The height and width of each transducer element is 0.452 [mm], and the distance between adjacent elements (in both axes) is 2.5 [m]. The overall width of the transducer is thus 2.9 [cm], and its overall height is 1.18 [cm].

The transmission frequency is 1.7 [MHz].

The beam pattern on transmit utilizes a single focal point located in the imaging plane, at a 6 [cm] distance from the center of the transducer. The beam pattern on receive is dynamic, matching the focal point to the current range.

No apodization is used, either on transmit or on receive.

Figure 5:
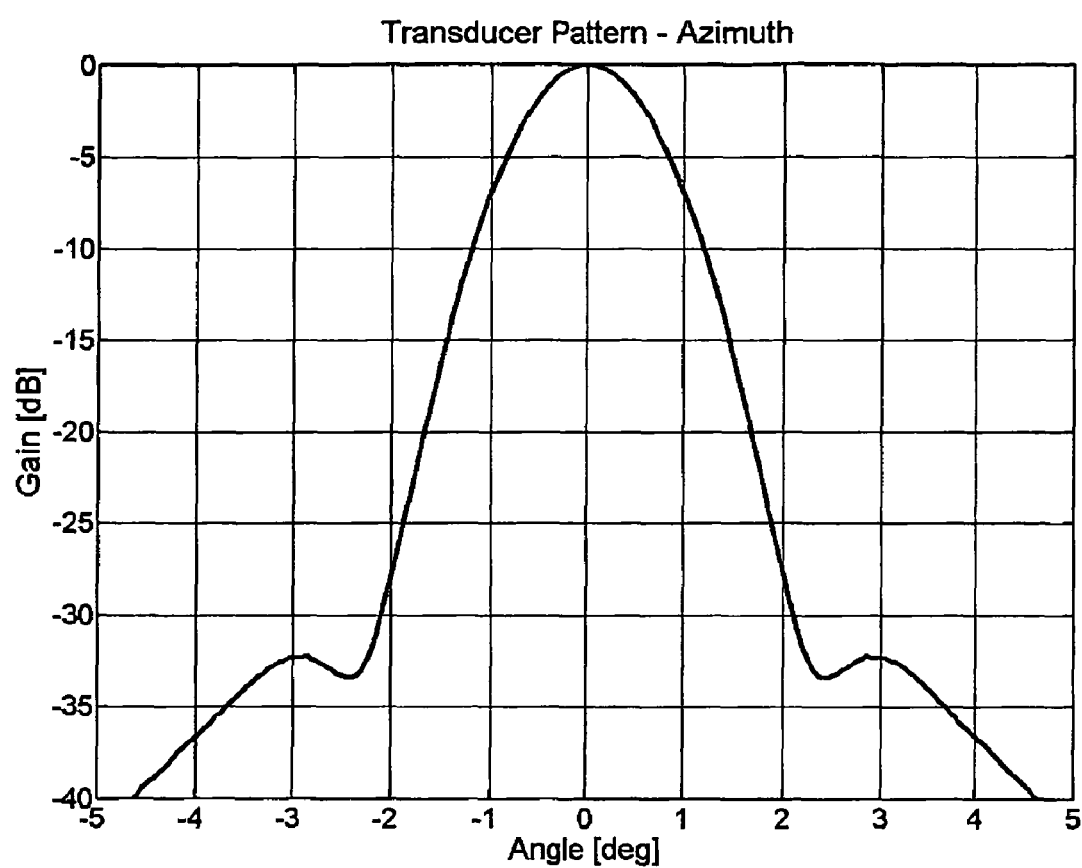
FIGS. 5-6 are plots that schematically show the two-way azimuth and elevation beam patterns of the transducer used in our simulations, in accordance with an embodiment of the present invention.
Figure 6:
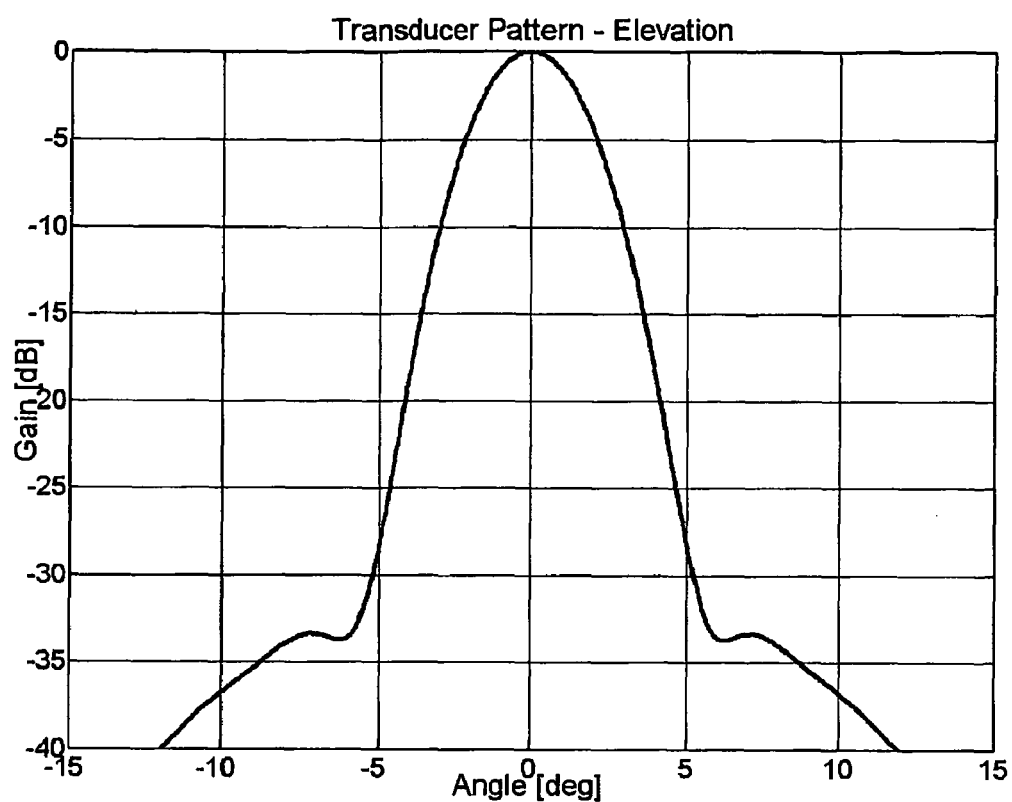

The resulting two-way azimuth beam pattern is shown in FIG. 5, and the two-way elevation beam pattern is shown in FIG. 6.

Two basic sets of simulations have been developed:
For visual illustration purposes, the clutter suppression method has been applied to a synthesized organ, whose ultrasonic image is affected by clutter. Two types of clutter have been considered:
Distributed clutter, simulating the effect of the lungs.
Strong localized clutter, simulating the effect of the ribcage.
In order to quantify the clutter residuals, the method's output has been calculated for two types of configurations:
Configurations including two reflectors—one representing the data of interest, and the other representing the clutter.
Configurations including two clutter sources, in addition to the object of interest.

All the results support the robustness and effectiveness of our method in various scenarios.

Visual Illustration—Distributed Clutter

In this set of simulations, our method has been applied to a synthesized organ, whose ultrasonic image is affected by distributed clutter. The scanned object is of elliptic shape, which is a rough approximation of the left ventricle.

Figure 7:
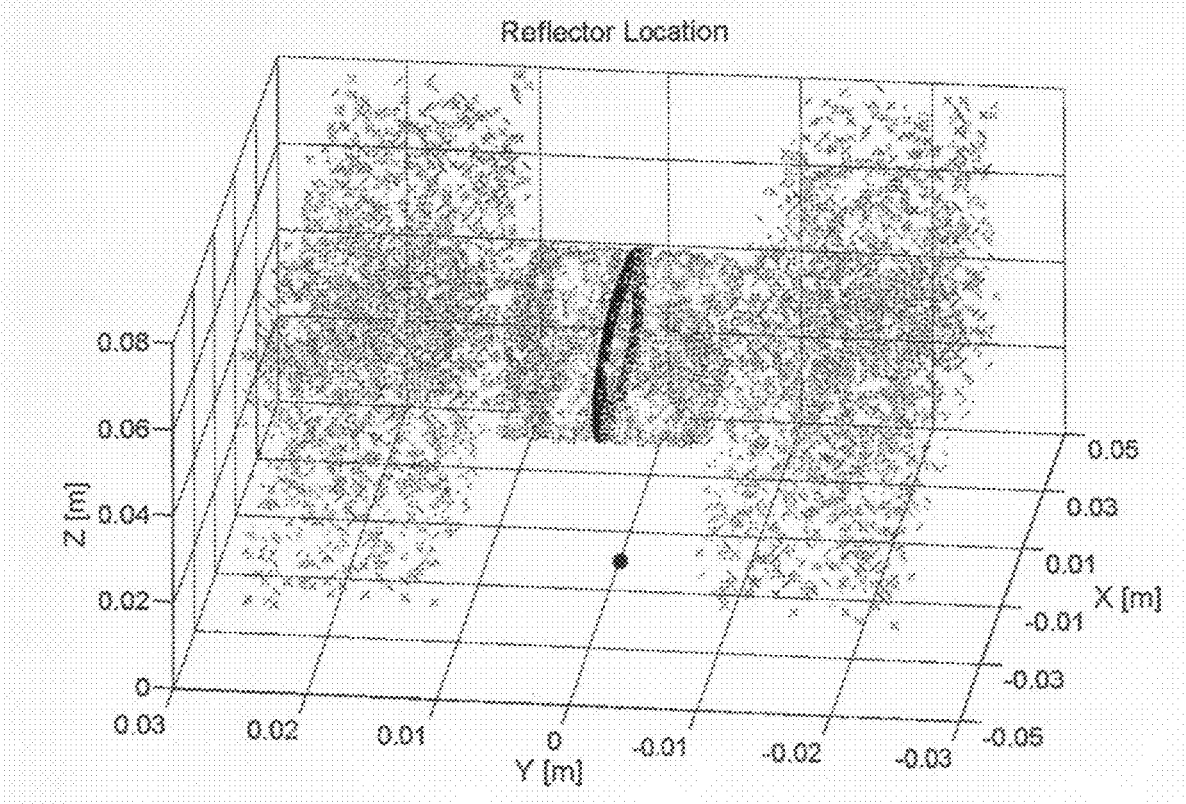
FIG. 7 describes a simulated scenario, used for visual demonstration of a method for suppressing clutter effects, in accordance with an embodiment of the present invention.

The simulated scenario is described in FIG. 7. The transducer (marked in FIG. 7 by a black dot on the bottom), is located at (0, 0, 0), and its broadside is parallel to the x-axis. 13000 point-like scatterers have been used:

5000 target scatterers (shown in FIG. 7 as black dots), located in the x-z plane (y=0).

3000 speckle scatterers (shown in FIG. 7 as gray circles), randomly placed above the target, between y=−0.75 [cm] and y=0.75 [cm].

5000 clutter scatterers (shown in FIG. 7 as gray crosses), randomly placed in the regions y∈[−2.5, −1] [cm] and y∈[1, 2.5] [cm].

The reflection coefficient of each target scatterer is 20, and the reflection coefficient of the clutter scatterers is 500±30. The reflection coefficient of the speckle scatterers is randomly set by the FIELD-II tool.

Figure 8:
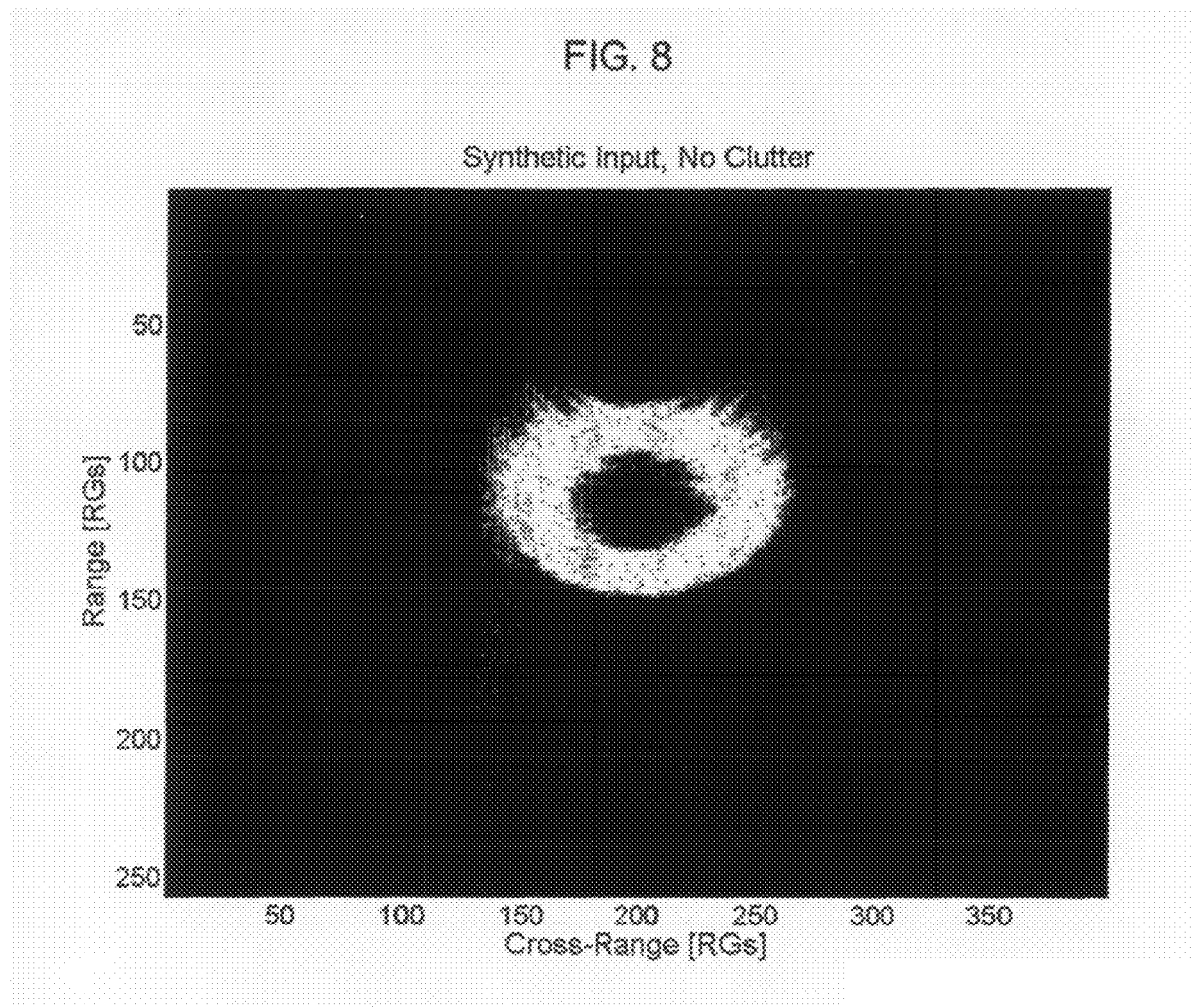
FIGS. 8-10 are simulated images that visually demonstrate a method for suppressing clutter effects, in accordance with an embodiment of the present invention.

The resulting image, in the absence of clutter, is displayed in FIG. 8. When the clutter is added, we obtain the image in FIG. 9. After applying our clutter suppression method, the result in FIG. 10 is achieved. Our procedure has significantly reduced the clutter level, while the object of interest shows no notable artifacts.

Figure 9:
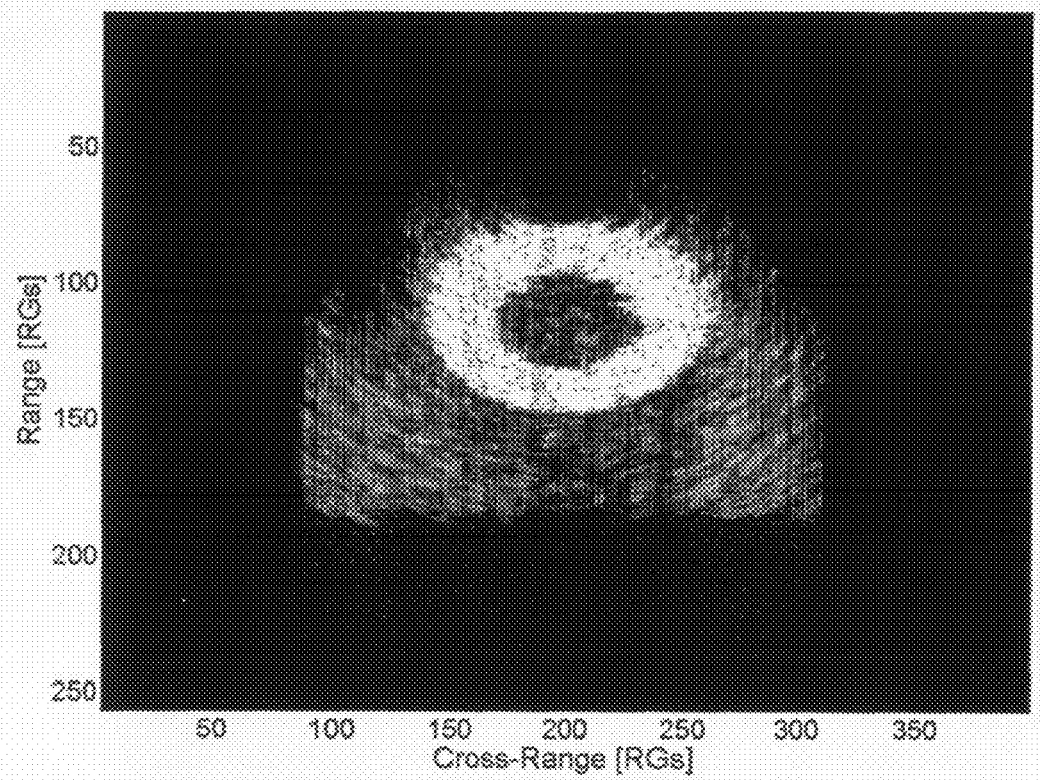
Figure 10:
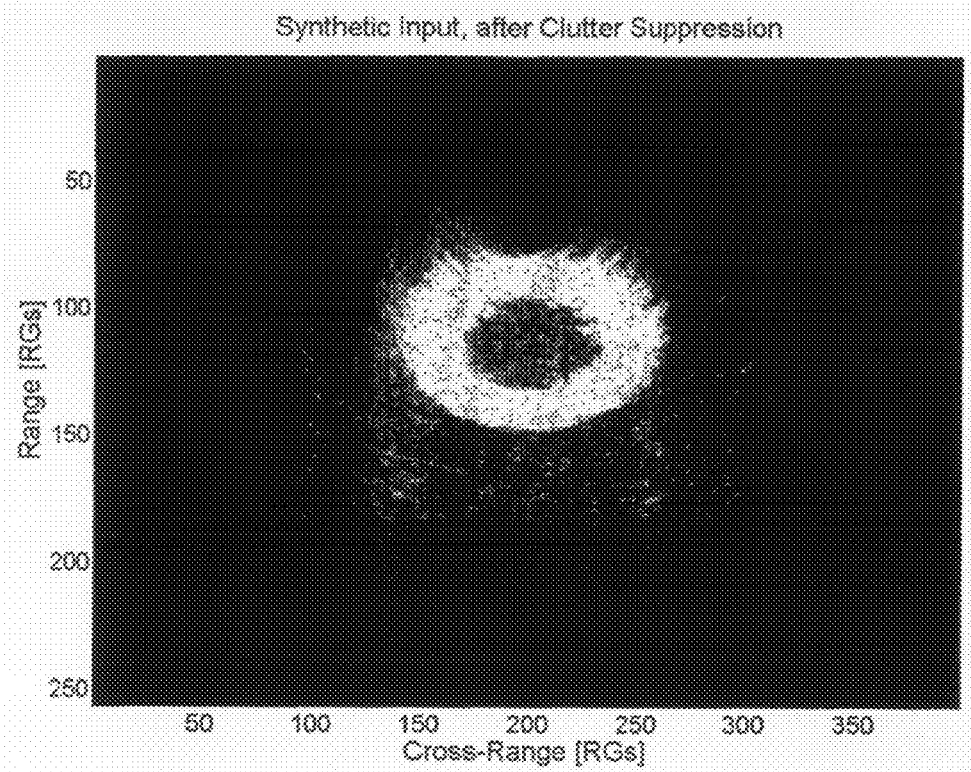

Note that FIGS. 8-10 have been created using a logarithmic Brightness Transfer Function (BTF). All the images have been normalized so as to assure that the mean videointensity of the target is the same for all cases.

In order to quantify the clutter suppression, we have defined the clutter suppression ratio:the ratio between the squared median of the signal magnitude before and after applying the clutter suppression procedure (the median is calculated over a large block outside the ellipse). The suppression ratio in the current configuration is 10 [dB], which seems adequate.

Visual Illustration—Strong Localized Clutter

This set of simulations uses the same synthesized organ in the presence of a different clutter source, which illustrates the effect of a single rib on echocardiographic images.

Figure 11:
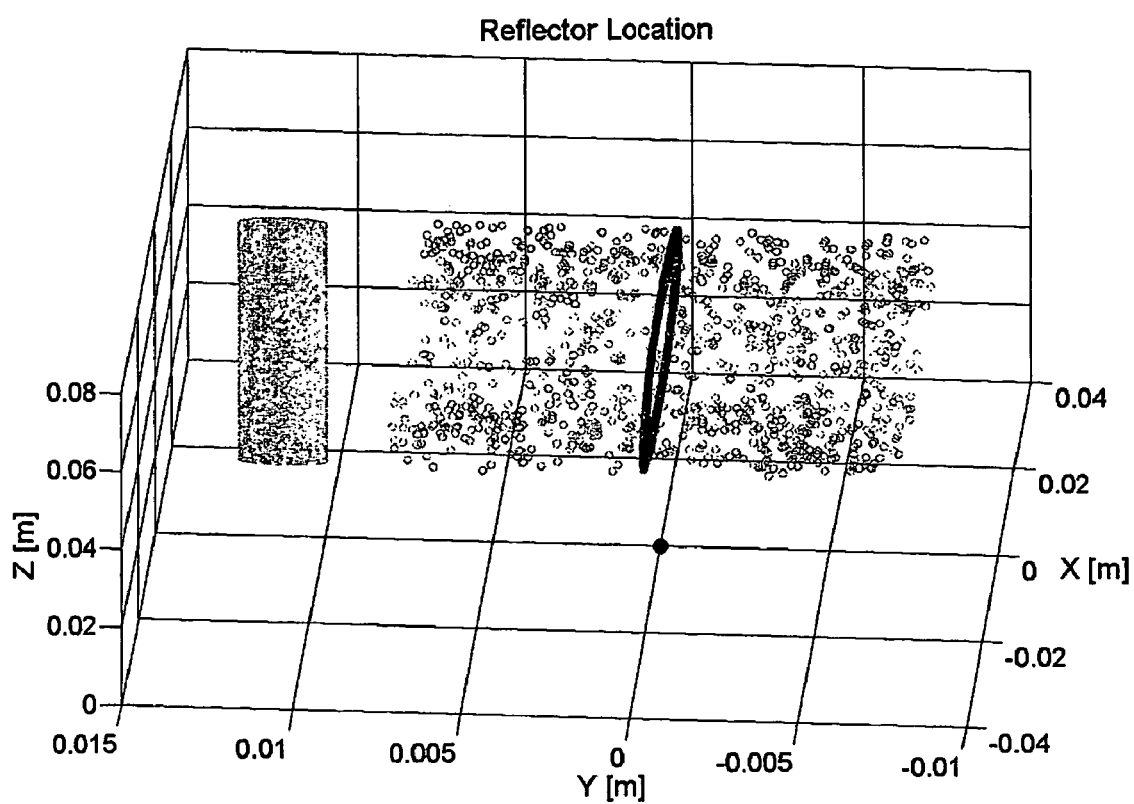
FIG. 11 describes an additional simulated scenario, used for visual demonstration of a method for suppressing clutter effects, in accordance with an embodiment of the present invention.

The simulated scenario is described in FIG. 11. In this case as well, the transducer (marked in FIG. 11 by a black dot on the bottom) is located at (0, 0, 0), and its broadside is parallel to the x-axis. The reflector configuration used here:
- 5000 target scatterers (shown in FIG. 11 as black dots), located in the x-z plane (y=0).
- 1000 speckle scatterers (shown in FIG. 11 as gray circles), randomly placed above the target, between y=−0.75 [cm] and y=0.75 [cm].
- 5490 clutter scatterers (shown in FIG. 11 as gray crosses), placed on 61 rings, whose radius is 0.125 [cm]. Each ring includes 90 reflectors, placed at equidistant angular locations. The centers of the rings are located at x=0, y=1.125 [cm], and z varies between 2 [cm] and 8 [cm] (z changes in increments of 0.1 [cm]).

The reflection coefficient of each target scatterer is 20, and the reflection coefficient of the clutter scatterers is 1000. The reflection coefficient of the speckle scatterers is randomly set by the FIELD-II tool.

We are aware of the fact that the resulting clutter source has a stronger effect than real-life clutter sources, but these parameters have been selected for demonstration purposes.

Figure 12:
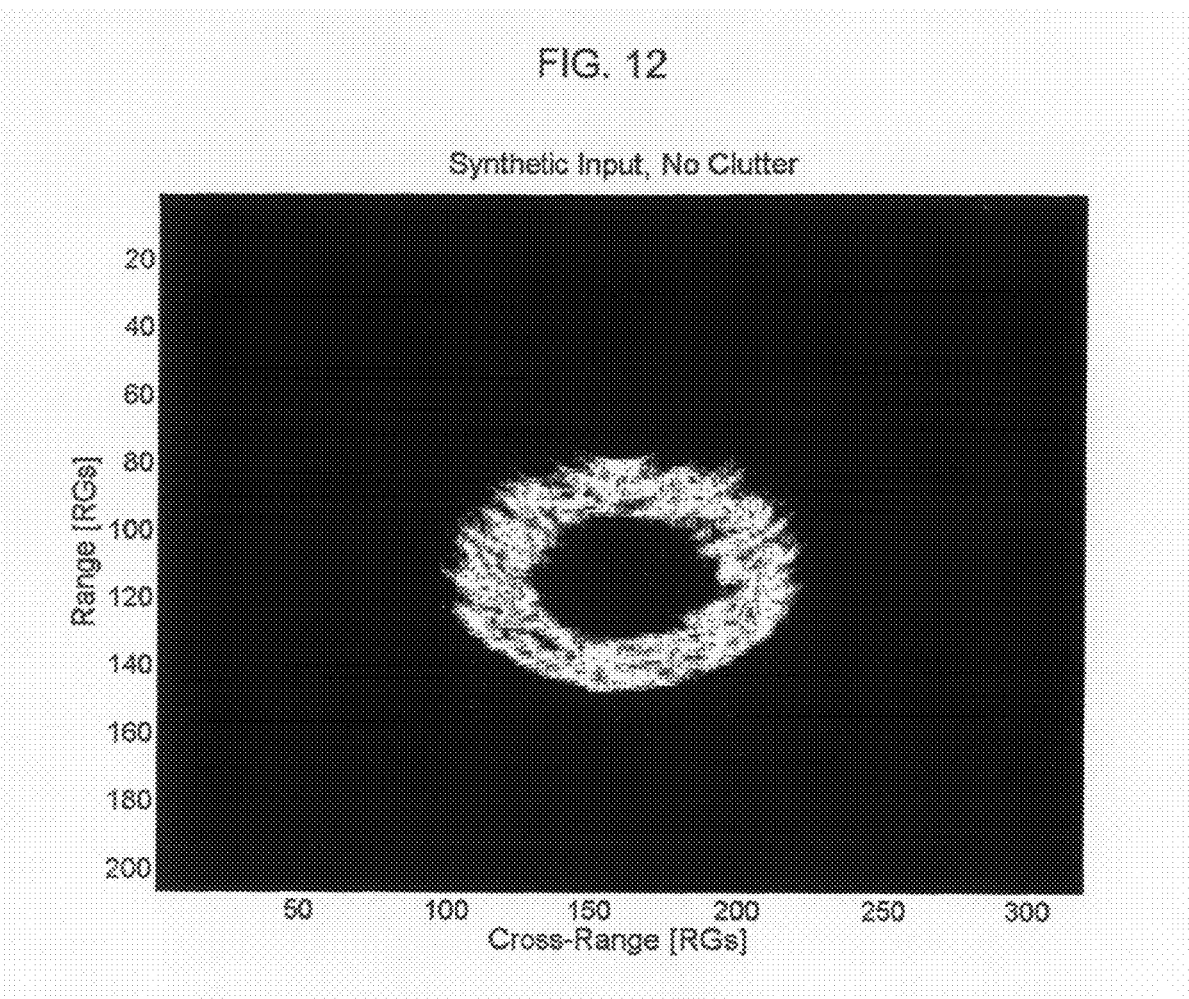
FIGS. 12-14 are additional simulated images that visually demonstrate a method for suppressing clutter effects, in accordance with an embodiment of the present invention.
Figure 13:
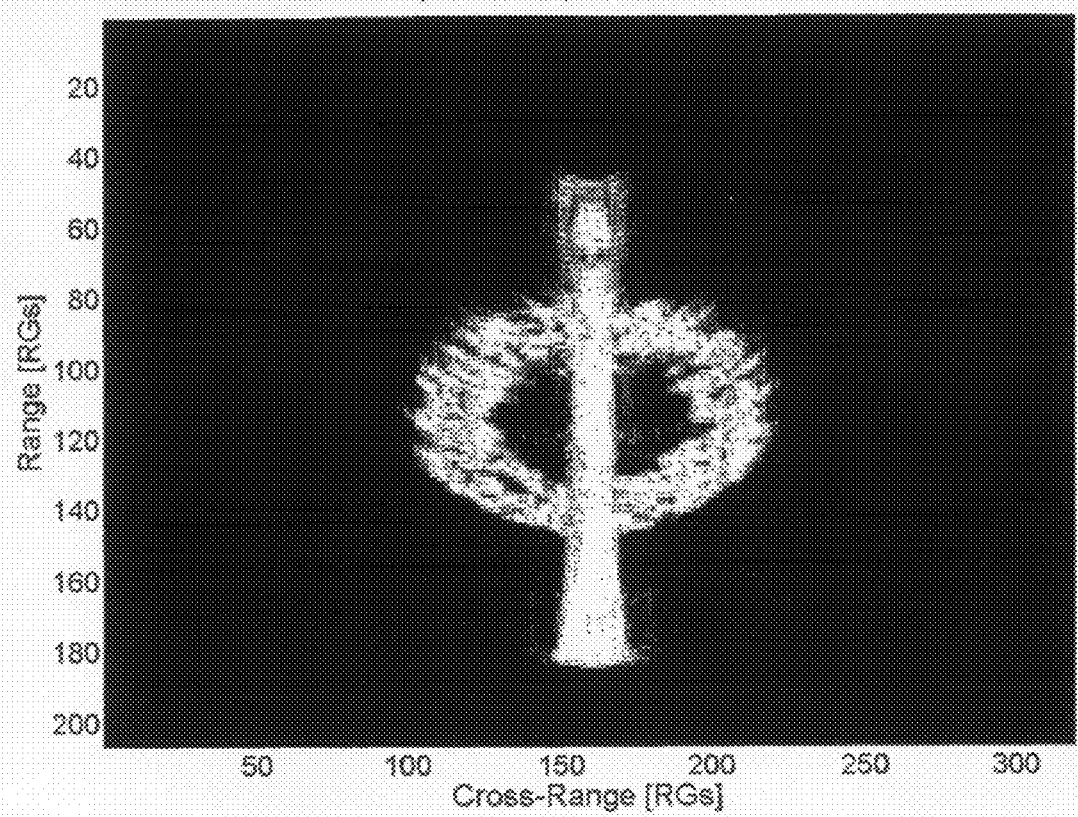
Figure 14:
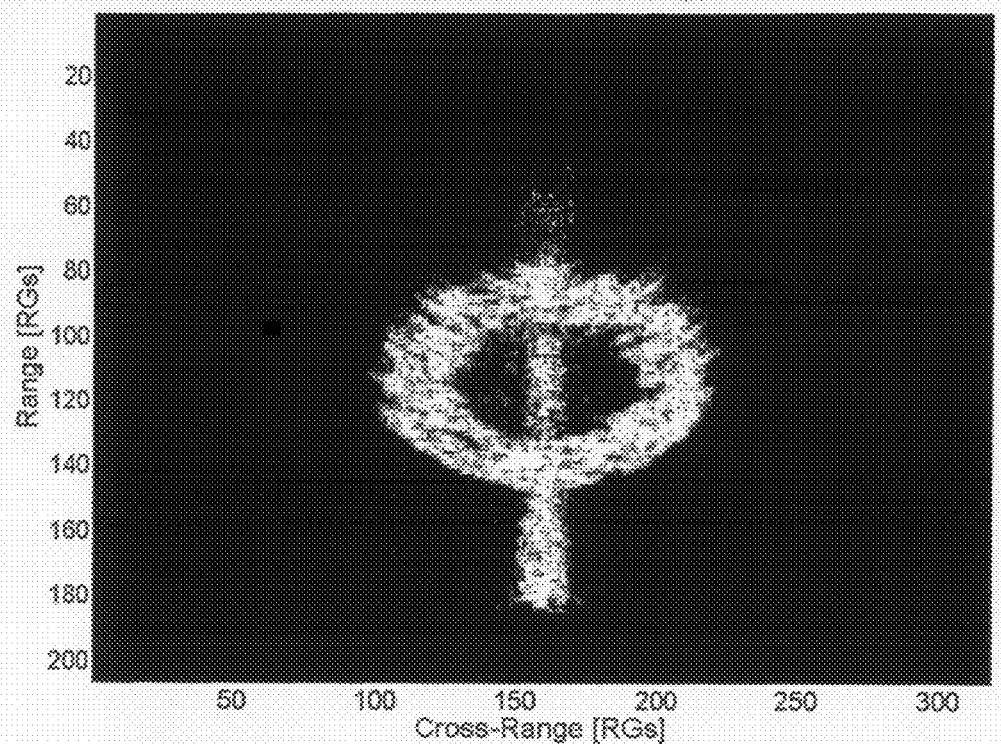

The resulting image, in the absence of clutter, is displayed in FIG. 12. When the clutter is added, we obtain the image in FIG. 13. The output of our clutter suppression algorithm is shown in FIG. 14. The clutter residuals in FIG. 14 have a much lower videointensity than the clutter in FIG. 13, and the suppression ratio is therefore high (13 [dB]). Furthermore, FIG. 14 may be used for the diagnosis of the bottom part of the synthetic organ, whereas the imaging quality in the corresponding region in FIG. 13 is insufficient for clinical diagnosis. These results further support the effectiveness of our technique.

Note that FIGS. 12-14 have also been created using a logarithmic BTF. All the images have been normalized so as to assure that the mean videointensity of the target is the same for all cases.

Clutter Suppression Quantification—A Single Clutter Source

In this group of simulations, the estimated signal before and after applying clutter suppression has been calculated for a set of two reflectors—one at the center of the region of interest, and the other (the clutter) at the same range, but at an angular difference of $\Delta\theta(\Delta\theta\epsilon[10°, 34°])$. The first reflector is point-like, whereas the second one is of varying width (between 0.1° and 5°, changing in increments of 0.1°). The reflection coefficient of the second reflector is approximately $10^5$ times greater than that of the first reflector.

Figure 15:
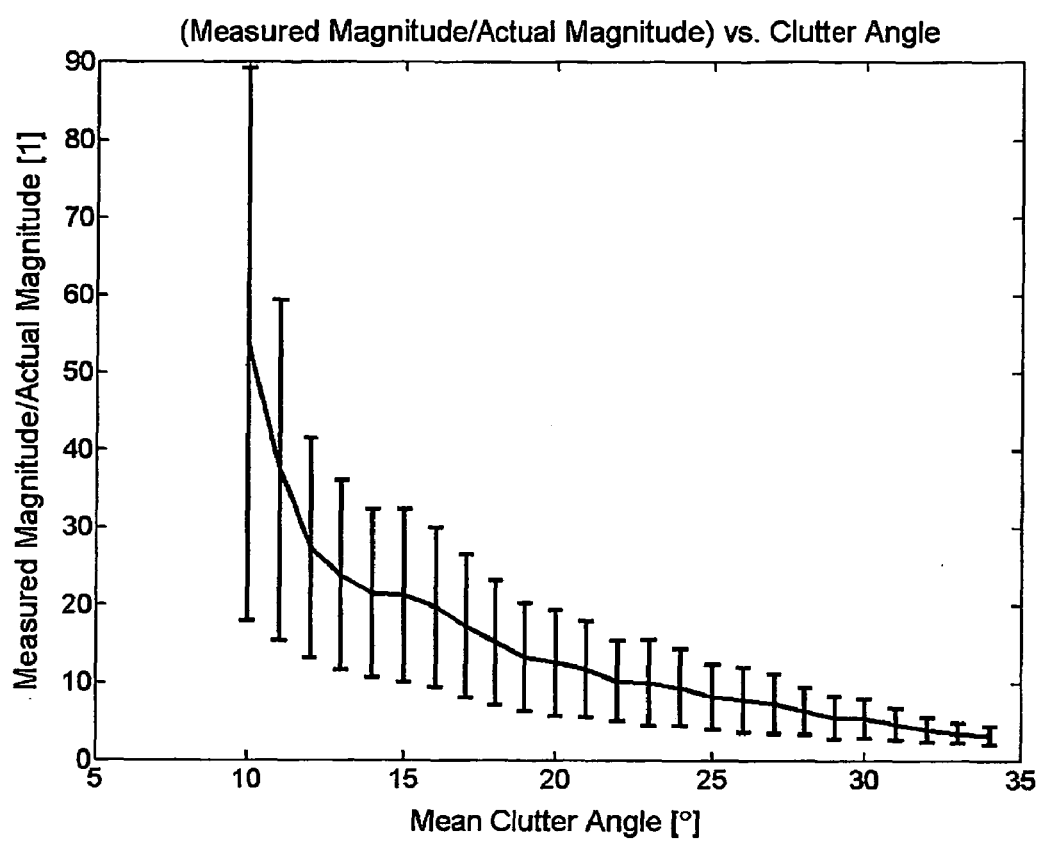
FIGS. 15-18 are plots that schematically show simulated signal magnitudes, in accordance with an embodiment of the present invention.
Figure 16:
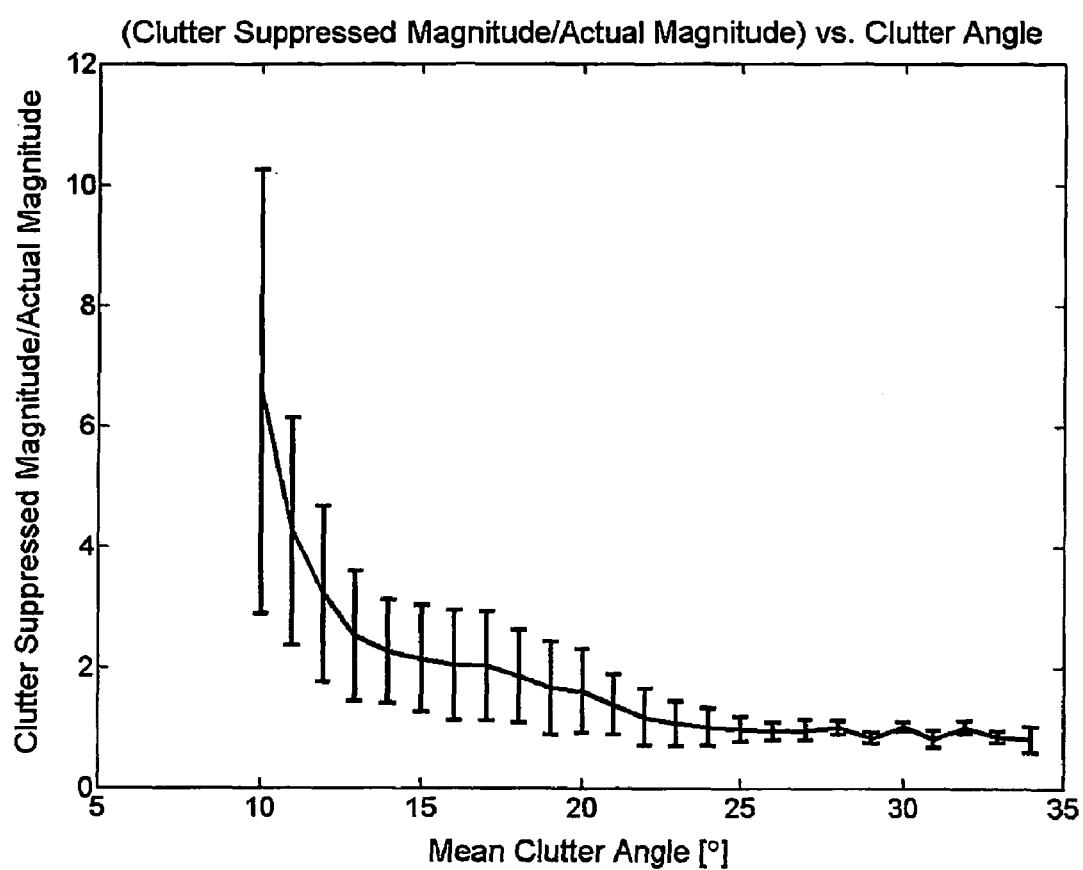
Figure 17:
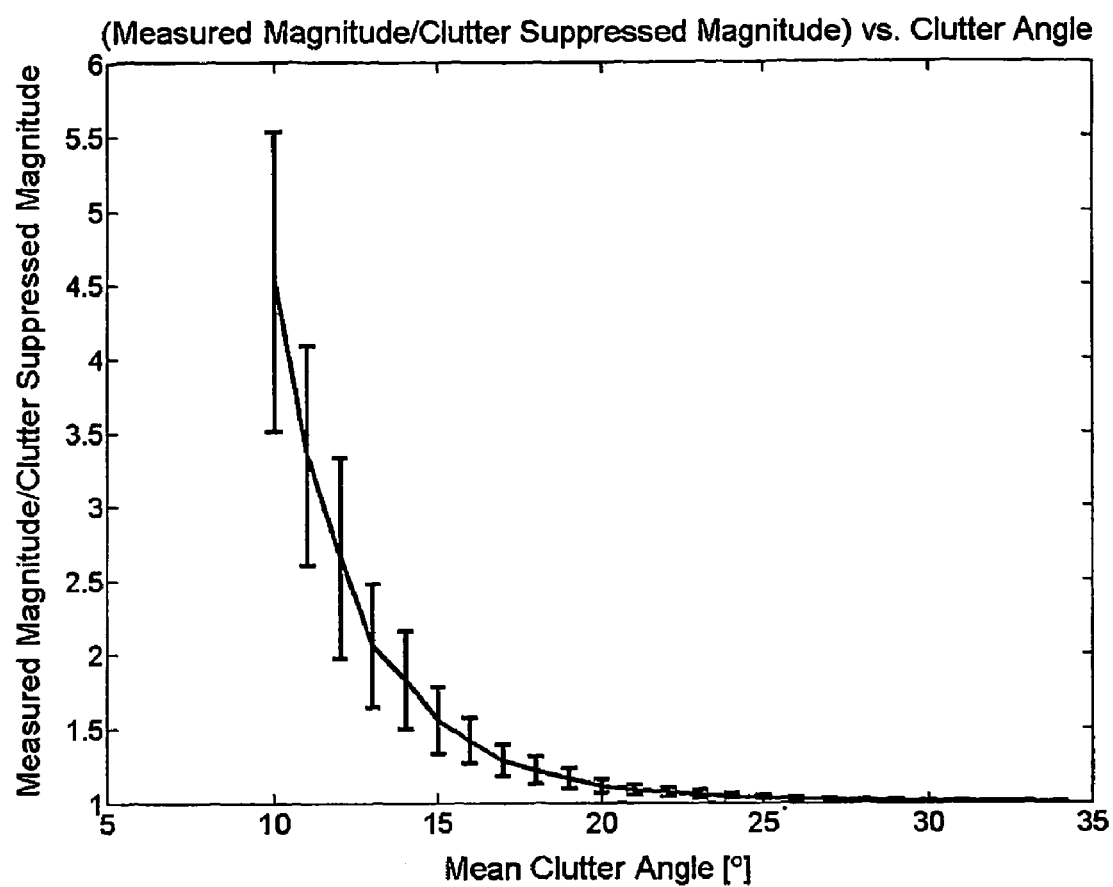
Figure 18:
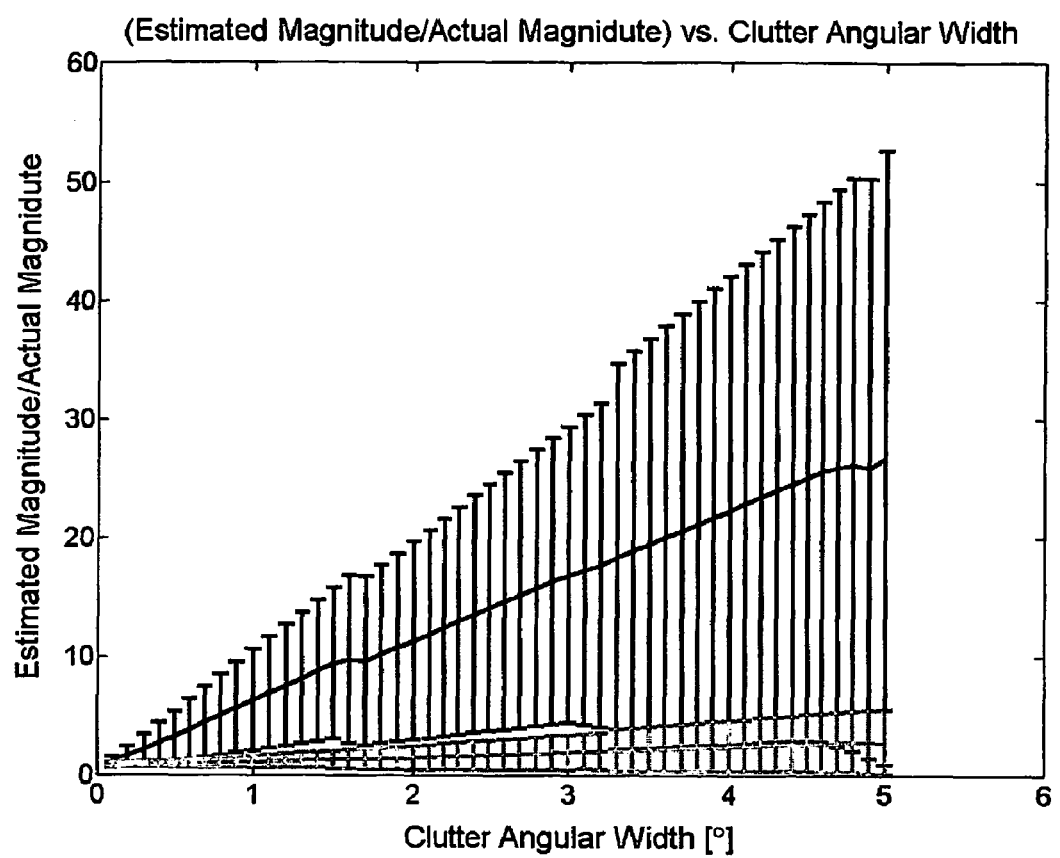

The results depend on two parameters—the angular difference $\Delta\theta$ and the angular width of the clutter. FIG. 15 shows the estimated signal magnitude, before clutter suppression, divided by the actual signal magnitude. FIG. 16 shows the estimated signal magnitude, after clutter suppression, divided by the actual signal magnitude. FIG. 17 shows the ratio between the signal magnitude before and after clutter suppression. In all three figures (FIGS. 15-17), the results are shown after averaging over the clutter's angular width, and the values appear as error-bars per $\Delta\theta$. FIG. 18 shows the magnitude of the estimated signal magnitude, before (in black) and after (in gray) clutter suppression, divided by the actual signal magnitude. The results are shown after averaging over the angular difference $\Delta\theta$, and the values appear as error-bars per angular width.

According to the results in FIGS. 15-18, the clutter suppression output is very close to the actual signal from the region of interest, whereas the measurements without clutter suppression are extremely different. These results demonstrate our procedure's capability to handle relatively wide clutter sources in various angular locations.

Clutter Suppression Quantification—A Dual Clutter Source

Figure 19:
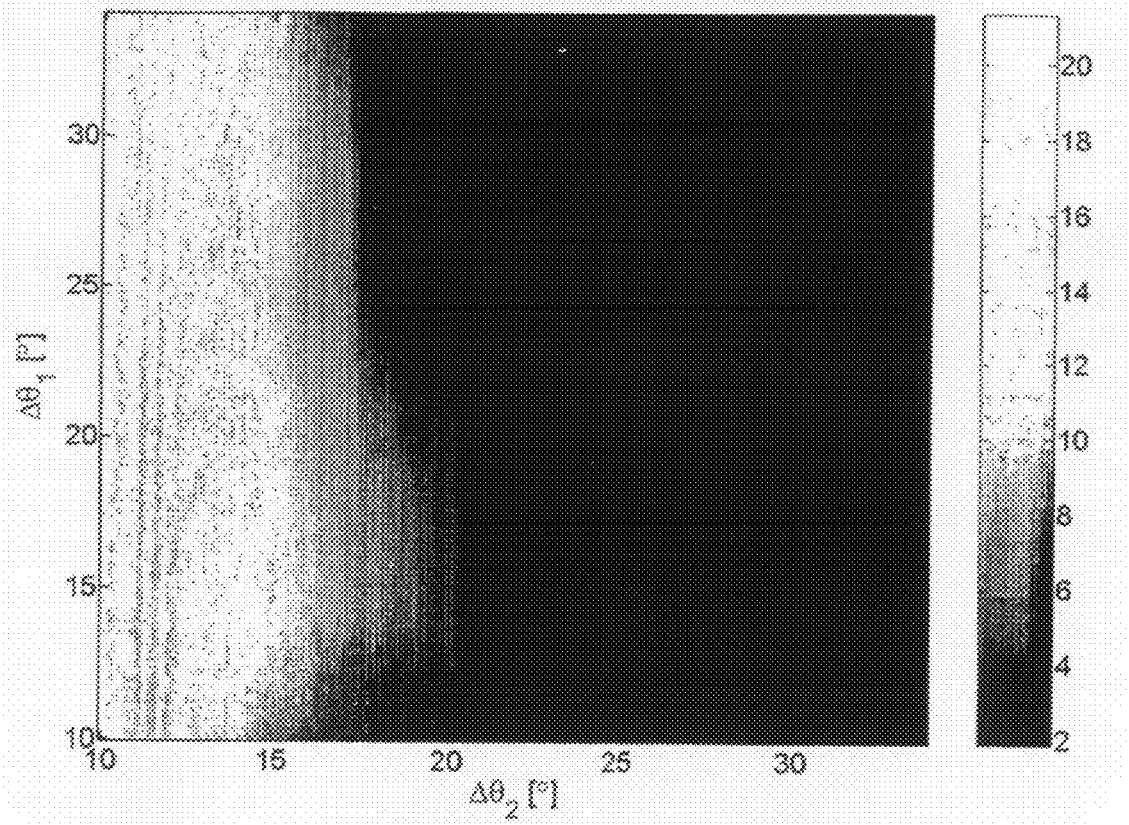
FIGS. 19-20 are two-dimensional graphs that schematically show simulated signal magnitudes, in accordance with an embodiment of the present invention.
Figure 20:
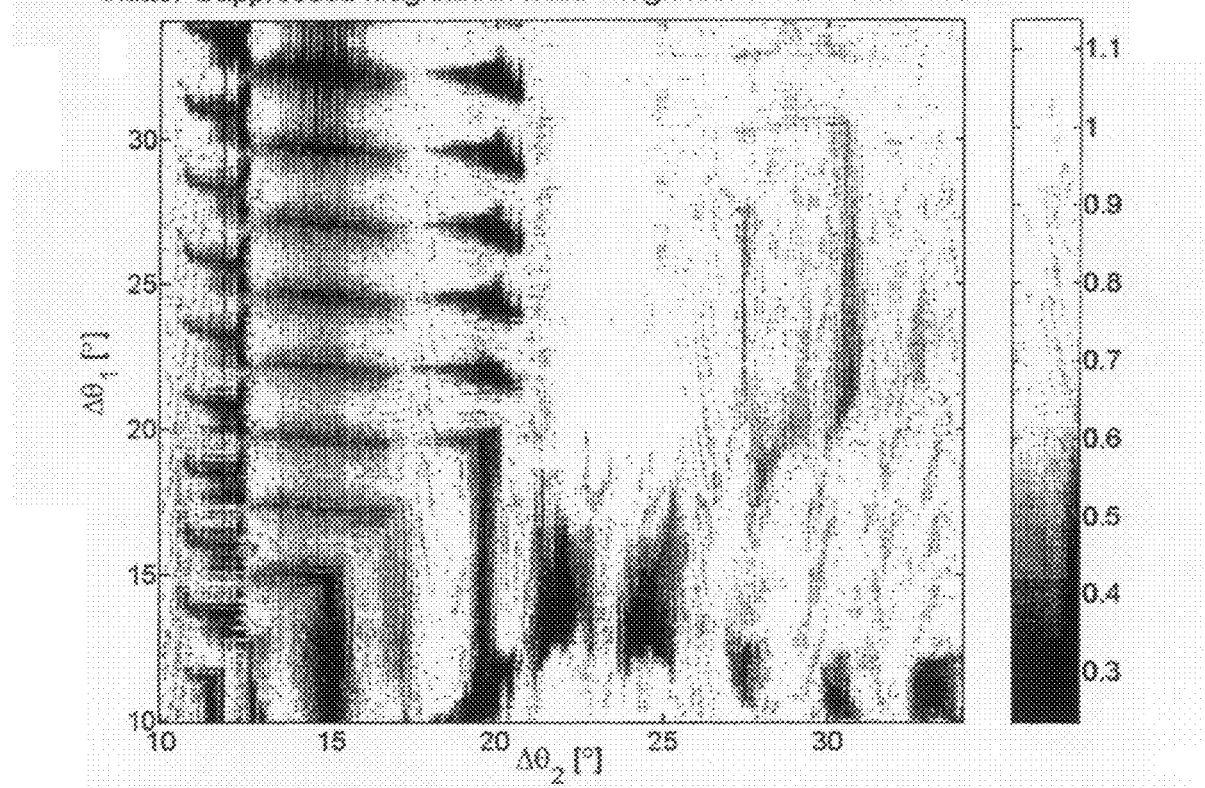

In these simulations, the estimated signal before and after clutter suppression has been calculated for a set of three reflectors—one at the center of the region of interest, and two (the clutter) at the same range, but at two different angles (the angular differences are $\Delta\theta_1$ and $\Delta\theta_2$ respectively). All reflectors are point-like, but with different reflection coefficients (the reflection coefficients of the two clutter reflectors are $10^4$ times and $10^5$ times greater than those of the first reflector, respectively). FIG. 19 shows the estimated signal magnitude before clutter suppression, divided by the actual signal magnitude. FIG. 20 shows the estimated signal magnitude after clutter suppression, divided by the actual signal magnitude. The results in FIGS. 19-20 are shown as a function of the angular location of the strong clutter reflector ($\Delta\theta_2$) and the weak clutter reflector ($\Delta\theta_1$). The value corresponding to each gray-level appears on the color bar, placed to the right of the image.

According to FIG. 19, the estimated signal magnitude before clutter suppression depends mostly on the strong reflector (i.e. the signal per $\Delta\theta_2$ varies only slightly with $\Delta\theta_1$), and is generally much higher than the actual signal magnitude. In contrast, the clutter suppression output (see FIG. 20) depends on the location of both reflectors, and is very similar, in most cases, to the correct signal. These results evidently show that the algorithm is agile, and may handle distributed clutter, as well as a single dominant clutter source.

Note that in most imaging platforms, the BTF used to translate the signal magnitude to the gray-level intensity is logarithmic rather than linear, so that even if the signal level after clutter suppression is only 25% of the actual relevant signal (which is the worst-case scenario here), the visual effect is not substantial.

APPENDIX 2

Theory of Ultrasonic Clutter Suppression

The general method described hereinbelow considers a probe comprising a main receiving channel and N auxiliary receiving channels. The clutter is suppressed by calculating a linear combination of the complex signal received by the main channel, denoted $V_M$, and the signals received from the N auxiliary channels denoted V, $V=(V_1, V_2, \ldots, V_N)^T$:

$$Z = V_M - W^T V$$

wherein W is a vector of complex weights, Z is the output signal, and the operator $^T$ indicates matrix transposition. The weight vector W is computed so as to provide maximum suppression, while having minimal effect on the desired signal received through the main-lobe of the main receiving channel. The clutter is regarded as samples of a stochastic process having a certain time autocorrelation function.

Therefore, the optimal weight vector W may be determined by minimizing the mean square prediction error, which equals the residual clutter power in the output signal, denoted $P_Z$:

$$P_Z = E(|Z|^2) = E(|V_M - W^T V|^2)$$

wherein $E(\cdot)$ denotes the statistical expectation. It can be shown that the solution to the optimization problem is given by:

$$W = cM^{-1}R$$

wherein c is an arbitrary constant value, $M^{-1}$ is the inverse of the N-dimensional covariance matrix of the set of samples V, and R is the N-dimensional covariance vector describing the relationship between $V_M$ and V:

$$M = E(V^* V^T)$$

$$R = E(V_M V^*)$$

(The Asterisk * Indicates Complex Conjugation.)

For the simple case of a single auxiliary beam and a single clutter signal, we obtain:

$$Z = V_M - W V_A$$

$$W = \frac{E(V_M V_A^*)}{E(|V_A|^2)}$$

wherein $V_A$ is the signal received through the auxiliary channel.

The derivation given above bears a formal similarity to the theory of side-lobe suppressers (SLC) in radar and communication systems. Further details of this theory are described, for example, by Farina in a book entitled "Antenna-Based Signal Processing for Radar Systems" (Artech House, January 1992), Chapter 4, pages 95-103, which is incorporated herein by reference.

The invention claimed is:

1. A method for ultrasonic imaging, comprising:
   transmitting ultrasonic radiation toward a target and receiving the ultrasonic radiation reflected from a region of the target so as to define a main reflected signal and an auxiliary reflected signal having different, respective main and auxiliary beam patterns;
   taking a difference between the main reflected signal and the auxiliary reflected signal so as to generate an output signal containing a reduced level of clutter in comparison with the main reflected signal
   organizing a magnitude of each of the main reflected and output signals into two dimensional arrays;
   establishing a y axis of a cell range and an x axis of a cell angle;
   determining at least one two-dimensional block defined by at least three cells along the y axis and by at least three cells along the x axis;
   defining a center cell within each at the least one two dimensional block; and
   determining a mean magnitude of the at least one block and calculating a ratio between the mean magnitude of the at least one block and the magnitude of the center cell for each of the magnitude of the main reflected signal array and the magnitude of the output signal array.

2. The method according to claim 1, including dividing the ratio of the magnitude ratio of the output signal array by the ratio of the magnitude of the main reflected signal array; and comparing the divided ratio with a threshold of the ratio of the output signal ratio and the main reflected signal ratio.

3. The method according to claim 2, including replacing the output signal magnitude by the main reflected signal magnitude for the center cell if the divided ratio exceeds the threshold.

4. A method for ultrasonic imaging, comprising:
   transmitting ultrasonic radiation toward a target and receiving the ultrasonic radiation reflected from a region of the target so as to define a main reflected signal and an auxiliary reflected signal having different, respective main and auxiliary beam patterns; and
   taking a difference between the main reflected signal and the auxiliary reflected signal so as to generate an output signal containing a reduced level of clutter in comparison with the main reflected signal;
   organizing a magnitude of each of the main reflected and output signals into two dimensional arrays;
   establishing a y axis of a cell range and an x axis of a cell cross range;
   determining at least one two-dimensional block defined by at least three cells along the y axis and by at least three cells along the x axis; and
   defining a center cell within each at the least one two dimensional block, and determining a mean magnitude of the at least one block and calculating a ratio between the mean magnitude of the at least one block and the magnitude of the center cell for each of the magnitude of the main reflected signal array and the magnitude of the output signal array.

5. The method according to claim 4, including dividing the ratio of the magnitude of the output signal array by the ratio of the magnitude of the main reflected signal array; and comparing the divided ratio with a threshold of the ratio of the output signal ratio and the main reflected signal ratio.

6. The method according to claim 5, including replacing the output signal magnitude by the main reflected signal magnitude for the center cell if the divided ratio exceeds the threshold.

7. A method for ultrasonic imaging, comprising:
   transmitting ultrasonic radiation toward a target and receiving the ultrasonic radiation reflected from a region of the target so as to define a main reflected signal and an auxiliary reflected signal having different, respective main and auxiliary beam patterns; and
   taking a difference between the main reflected signal and the auxiliary reflected signal so as to generate an output signal containing a reduced level of clutter in comparison with the main reflected signal;
   organizing a magnitude of each of the main reflected and output signals into three dimensional arrays;
   establishing a y axis of a cell range, an x axis of a cell angle in azimuth and a z axis of a cell angle in elevation;

determining at least one three dimensional block defined by at least three cells along the x, y and z-axes;

defining a center cell within each at least one three dimensional block; and determining a mean magnitude of the at least one three dimensional block and calculating a ratio between the mean magnitude of the at least one three dimensional block and the magnitude of the center cell for each of the magnitude of the main reflected signal array and the magnitude of the output signal array.

8. The method according to claim 7, including dividing the ratio of the magnitude of the output signal array by the ratio of the magnitude of the main reflected signal array; and comparing the divided ratio with a threshold of the ratio of the output signal ratio and the main reflected signal ratio.

9. The method according to claim 8, including: replacing the output signal magnitude by the main reflected signal magnitude for the center cell if the divided ratio exceeds the threshold.

10. A method for ultrasonic imaging, comprising:

transmitting ultrasonic radiation toward a target and receiving the ultrasonic radiation reflected from a region of the target so as to define a main reflected signal and an auxiliary reflected signal having different, respective main and auxiliary beam patterns; and taking a difference between the main reflected signal and the auxiliary reflected signal so as to generate an output signal containing a reduced level of clutter in comparison with the main reflected signal;

organizing a magnitude of each of the main reflected and output signals into three dimensional arrays;

establishing a y axis of a cell range, an x axis of a cell cross range in azimuth and a z axis of a cell cross range in elevation;

determining at least one three dimensional block defined by at least three cells along the x, y and z-axes;

defining a center cell within each at least one tree dimensional block; and determining a mean magnitude of the at least one three dimensional block and calculating a ratio between the mean magnitude of the at least one three dimensional block and the magnitude of the center cell for each of the magnitude of the main reflected signal array and the magnitude of the output signal array.

11. The method according to claim 10, including dividing the ratio of the magnitude of the output signal array by the ratio of the magnitude of the main reflected signal array; and comparing the divided ratio with a threshold of the ratio of the output signal ratio and the main reflected signal ratio.

12. The method according to claim 10, including: replacing the output signal magnitude by the main reflected signal magnitude for the center cell if the divided ratio exceeds the threshold.

13. A computer software product for use in conjunction with a probe, which transmits ultrasonic radiation toward a target and generates signals in response to the ultrasonic radiation reflected from a region of the target, the product comprising a computer-readable non-transitory medium in which program instructions are stored, which instructions, when read by a computer, cause the computer to: process the signals so as to define a main reflected signal and an auxiliary reflected signal having different, respective main and auxiliary beam patterns, to take a difference between the main reflected signal and the auxiliary reflected signal so as to generate an output signal containing a reduced level of clutter in comparison with the main reflected signal, to organize a magnitude of each of the main reflected and output signals into two dimensional arrays, to establish a y axis of a cell range and an x axis of a cell angle, to determine at least one two-dimensional block defined by at least three cells along the y axis and by at least three cells along the x axis, to define a center cell within each at the least one two dimensional block, and determine a mean magnitude of the at least one block and calculating a ratio between the mean magnitude of the at least one block and the magnitude of the center cell for each of the magnitude of the main reflected signal array and the magnitude of the output signal array.

14. A method for ultrasonic imaging, comprising:

transmitting an ultrasonic radiation towards a target tissue;

receiving reflections of the ultrasonic radiation from a region of the target in a main reflected signal and one or more auxiliary reflected signals, wherein each one of the reflected signals is associated with a different and distinct beam pattern, wherein all of the reflected signals have an identical frequency;

determining a de-correlation time of at least one of: the main reflected signal and the one or more auxiliary reflected signals;

applying a linear combination to the main reflected signal and the one or more auxiliary reflected signals, to yield an output signal with reduced clutter, wherein the linear combination comprises a plurality of complex numbers weights that are being determined for each angle and for each range within the target tissue, wherein each complex number weight is selected such that each estimated reflection due to the clutter is nullified, wherein a reflection is determined as associated with clutter if the determined de-correlation time is above a specified threshold.

15. The method according to claim 14, wherein receiving the ultrasonic radiation comprises receiving the reflected ultrasonic radiation using an array of transducers, and multiplying outputs of the transducers by respective first and second pluralities of apodization coefficients, in accordance with the main and auxiliary beam patterns, in order to define the main and auxiliary reflected signals.

16. The method according to claim 14, wherein receiving the ultrasonic radiation comprises defining a plurality of auxiliary reflected signals.

17. The method according to claim 14, wherein the main beam pattern is narrower than the auxiliary beam pattern.

18. The method according to claim 14, wherein taking the difference comprises:

calculating a complex weight responsively to the reflected signals;

multiplying the auxiliary received signal by the complex weight to obtain a result; and subtracting the result from the main reflected signal so as to produce the output signal.

19. The method according to claim 18, wherein calculating the complex weight comprises averaging the reflected signals over multiple image frames, and determining the complex weight based on the averaged reflected signals.

20. The method according to claim 18, wherein calculating the complex weight comprises taking a minimum value of the reflected signals over multiple image frames, and determining the complex weight based on the minimum value.

21. The method according to claim 18, wherein multiplying the auxiliary received signal by the complex weight and subtracting the result comprise determining a combined beam pattern responsively to the complex weight and to the main and auxiliary beam patterns, and applying the combined beam pattern to the main reflected signal.

22. The method according to claim 18, wherein receiving the ultrasonic radiation comprises collecting the reflected ultrasonic radiation in each image frame at multiple different settings of range and angle, and wherein calculating the complex weight comprises calculating a respective complex weight value for each of the different settings of the range and angle.

23. The method according to claim 14, wherein taking the difference comprises calculating a phase difference between the main reflected signal and the auxiliary reflected signal, and forcing a null at an angle responsive to the phase difference in an effective beam pattern corresponding to the output signal.

24. The method according to claim 23, wherein forcing the null comprises forcing the null only if the angle is within a predetermined range.

25. The method according to claim 14, and comprising generating an improved image responsively to the output signal and displaying the improved image to a user.

26. The method according to claim 14, wherein the output signal has a reduced dynamic range relative to the main reflected signal.

27. The method according to claim 14 including:
normalizing a magnitude of the main reflected signal to a magnitude of the output signal; and
taking a minimum value per cell between the magnitude of the main reflected signal and the magnitude of the output signal.

28. An apparatus for ultrasonic imaging, comprising:
a probe, which is adapted to transmit an ultrasonic radiation towards a target tissue, at a specific beam pattern; and
a scanner adapted to:
receive reflections of the ultrasonic radiation from a region of the target in a main reflected signal and one or more auxiliary reflected signals, wherein each one of the reflected signals is associated with a different and distinct beam pattern, wherein all of the reflected signals have an identical frequency;
determine a de-correlation time of at least one of: the main reflected signal and the one or more auxiliary reflected signals; and
apply a linear combination to the main reflected signal and the one or more auxiliary reflected signals, to yield an output signal with reduced clutter, wherein the linear combination comprises a plurality of complex numbers weights that are being determined for each angle and for each range, wherein each complex number weight is selected such that each estimated reflection due to the clutter is nullified, wherein a reflection is determined as associated with the clutter if the determined de-correlation time is above a specified threshold.

29. The apparatus according to claim 28, wherein the probe comprises an array of ultrasonic transducers, and wherein the scanner is adapted to multiply outputs of the transducers by respective first and second pluralities of apodization coefficients in accordance with the main and auxiliary beam patterns, in order to define the main and auxiliary reflected signals.

30. The apparatus according to claim 28, wherein the scanner is adapted to define a plurality of auxiliary reflected signals.

31. The apparatus according to claim 28, wherein the main beam pattern is narrower than the auxiliary beam pattern.

32. The apparatus according to claim 28, wherein the scanner is adapted to calculate a complex weight responsively to the reflected signals, to multiply the auxiliary received signal by the complex weight in order to obtain a result, and to subtract the result from the main reflected signal so as to produce the output signal.

33. The apparatus according to claim 32, wherein the scanner is adapted to average the reflected signals over multiple image frames and to determine the complex weight based on the averaged reflected signals.

34. The apparatus according to claim 32, wherein the scanner is adapted to take a minimum value of the reflected signals over multiple image frames, and to determine the complex weight based on the minimum value.

35. The apparatus according to claim 32, wherein the scanner is adapted to apply a combined beam pattern to the main reflected signal, wherein the combined beam pattern is determined responsively to the complex weight and to the main and auxiliary beam patterns.

36. The apparatus according to claim 32, wherein the scanner is adapted to collect the reflected ultrasonic radiation in each image frame at multiple different settings of range and angle and to calculate a respective complex weight value for each of the different settings of the range and angle.

37. The apparatus according to claim 28, wherein the scanner is adapted to calculate a phase difference between the main reflected signal and the auxiliary reflected signal, and to force a null at an angle responsive to the phase difference in an effective beam pattern corresponding to the output signal.

38. The apparatus according to claim 37, wherein the scanner is adapted to force the null only if the angle is within a predetermined range.

39. The apparatus according to claim 28, wherein the scanner is adapted to generate an improved image responsively to the output signal, and comprising a display unit, which is adapted to display the improved image to a user.

40. The apparatus according to claim 28, wherein the output signal has a reduced dynamic range relative to the main reflected signal.

* * * * *